(12) United States Patent
Lahann et al.

(10) Patent No.: US 7,648,739 B2
(45) Date of Patent: Jan. 19, 2010

(54) SWITCHABLE SURFACES

(75) Inventors: Joerg Lahann, Arlington, MA (US); Samir S. Mitragotri, Goleta, CA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/390,405

(22) Filed: Mar. 27, 2006

(65) Prior Publication Data

US 2006/0263033 A1 Nov. 23, 2006

Related U.S. Application Data

(62) Division of application No. 10/284,794, filed on Oct. 31, 2002, now Pat. No. 7,020,355.

(60) Provisional application No. 60/350,090, filed on Nov. 2, 2001.

(51) Int. Cl.
*C08J 7/04* (2006.01)
(52) U.S. Cl. .................. 427/516; 385/16; 385/151; 385/153; 435/283.1; 435/287.1; 436/518; 427/2.11; 427/457; 427/487
(58) Field of Classification Search .......... 435/6, 435/91.2, 7.1; 536/22.1, 23.1, 24.3; 530/412
See application file for complete search history.

(56) References Cited

U.S. PATENT DOCUMENTS

| | | | |
|---|---|---|---|
| 3,558,920 A | 1/1971 | Giaever | |
| 4,079,407 A | 3/1978 | Hudson | |
| 5,512,131 A | 4/1996 | Kumar et al. | |
| 5,797,898 A | 8/1998 | Santini, Jr. et al. | |
| 6,031,756 A | 2/2000 | Gimzewski et al. | |
| 6,054,752 A | 4/2000 | Hara et al. | |
| 6,198,655 B1 | 3/2001 | Heath et al. | |
| 6,287,765 B1 * | 9/2001 | Cubicciotti | 435/6 |
| 6,548,841 B2 | 4/2003 | Frazier et al. | |
| 6,582,807 B2 | 6/2003 | Baer | |
| 6,762,025 B2 | 7/2004 | Cubicciotti | |
| 6,867,427 B2 | 3/2005 | Zhang et al. | |

(Continued)

FOREIGN PATENT DOCUMENTS

DE 19604173 8/1997

(Continued)

OTHER PUBLICATIONS

Abbott, et al., "Reversible Wettability of Photoresponsive Pyrimidine-Coated Surfaces", Langmuir, 15: 8923-8928, 1999.

(Continued)

*Primary Examiner*—Nelson Yang
(74) *Attorney, Agent, or Firm*—Wolf, Greenfield & Sacks, P.C.; C. Hunter Baker

(57) ABSTRACT

A substrate having a surface with reversibly switchable properties. The surface comprises a nanolayer of a material that switches from a first conformation state to a second conformation state when an external stimulus is applied. When the nanolayer is in the first conformation state, the surface is characterized by a first property, and when the nanolayer is in the second conformation state, the surface is characterized by a second property.

10 Claims, 13 Drawing Sheets

U.S. PATENT DOCUMENTS

| | | | |
|---|---|---|---|
| 6,995,312 | B2 | 2/2006 | Zhou et al. |
| 2001/0003621 | A1* | 6/2001 | Jiang et al. ................. 428/447 |
| 2001/0018923 | A1 | 9/2001 | Zuppero et al. |
| 2005/0089890 | A1 | 4/2005 | Cubicciotti |

FOREIGN PATENT DOCUMENTS

| | | |
|---|---|---|
| DE | 19905792 | 8/2000 |
| DE | 19905795 | 12/2000 |
| EP | 1095694 | 8/2008 |
| WO | 99/63329 | 12/1999 |
| WO | 00/32044 | 6/2000 |

OTHER PUBLICATIONS

Abraham, "Thermodynamics of Solution of Homologous Series of Solutes in Water", J. Chem. Soc., Faraday Trans. 80: 153-181, 1984.

Anderson, et al., "Effects of Applied Potential Upon the In Situ Structure Of Self-Assembled Monolayers on Gold Electrodes", Langmuir, 10: 1638-1641, 1994.

Aydogan, et al., "A Molecular-Thermodynamic Model for Gibbs Mobolayers Formed from Redox-Active Surfactants at the Surfaces of Aqueous Solutions: Redox-Induced Changes in Surface Tension", Langmuir, 15: 722-730, 1999.

Baldelli, et al., "Sum Frequency Generation of CO On (111) and Polycrystalline Platinum Electrode Surfaces: Evidence for SFG Invisible Surface CO", J. Phys. Chem. 103: 8920-8925, 1999.

Boden, et al., "Triphenylene-Based Discotic Liquid Crystals as Self-Assembled Monolayers", Langmuir, 15:3790-3797, 1999.

Byloos, et al., "Phase Transitions of Alkanethiol Self-Assembled At an Electrified Gold Surface," J. Phys. Chem. B, 105: 5900-5905, 2001.

Chaudhury, et al., "How to Make Water Run Uphill", Science, 256: 1539-1541, 1992.

Chidsey, et al., "Chemical Functionality in Self-Assembled Monolayers: Structural and Electrochemical Properties", Langmuir, 6: 682-691, 1990.

Cornell, et al., "A Second Generation Force Field for the Simulation of Protein, Nucleic Acids, and Organic Molecules", J. Am. Chem. Soc. 117: 5179-5197, 1995.

Decher, et al., "Buildup of Ultrathin Multilayer Films by a Self-Assembly Process: II. Consecutive Adsorption of Anionic and Cationic Bipolar Amphiphiles and Polyelectrolytes on Charged Surfaces" Bes. Bunsenges. Phys. Chem. 95: 1430, 1991.

Decher, et al., "Fuzzy Nanoassemblies: Toward Layered Polymeric Multicomposites", Science, 277: 1232-1237, 1997.

De Crevoisier, et al., "Switchable Tackiness and Wettability of a Liquid Crystalline Polymer", Science, 285: 1246-1249, 1999.

DeGennes, "Wetting: Statistics and Dynamics", Rev. Mod. Phys. 57: 827-863, 1985.

Everett, et al., "Factors That Influence Stability of Self-Assembled Organothiols on Gold Under Electrochemical Conditions", Anal. Chim. Acta, 307: 253-268, 1995.

Finklea, et al., "Blocking Orientated Monolayers of Alkyl Mercaptans on Gold Electrodes", Langmuir, 3: 409-413, 1987.

Gallardo, et al., "Electrochemical Principles for Active Control of Liquids on Submillimeter Scales", Science, 283: 57-60, 1999.

Hines, et al., Conformation of Alkanethiols On Au, (111) and Pt(111) Electrodes: A Vibrational Spectroscopy Study, Langmuir, 11: 493-497, 1995.

Ichimura, et al., "Light-Driven Motion of Liquids on a Photoresponsive Surface", Science, 288: 1624-1626, 2000.

Lahann, et al., "A New Method Toward Micro-engineered Surfaces Based on Reactive Coating", Angew. Chem. Int. Ed. 40: 3166-3169, 2001.

Li, et al., "Relationship Between Packing Structure and Headgroups of Self-Assembled Monolayers On Au (111): Bridging Experimental Observations Through Computer Simulations", J. Phys. Chem. B. 102: 2935-2946, 1998.

Nuzzo, et al., "Fundamental Studies of Microscopic Wetting on Organic Surfaces, 1. Formation and Structural Characterization of a Self-Consistent Series of Polyfunctional Organic Monolayers", J. Am. Chem. Soc. 112: 558-569, 1990.

Ong, et al., "Sum-Frequency Spectroscopy of Monolayers of Alkoxy-Terminated Alkanethiols in Contact with Liquids", Langmuir, 9: 1836-1845, 1993.

Schoenfisch, et al., "Effects of Electrolyte and Potential on the In Situ Structure of Alkanethiol Self-Assembled Monolayers on Silver", Langmuir, 15: 509-517, 1999.

Shen, "Surface Properties Probed by Second-Harmonic And Sum-Frequency Generation", Nature, 337: 519-525, 1989.

Shon, et al., "Low Density Self-Assembled Monolayers on Gold Derived from Chelating 2-Monoalkylpropane-1,3-Dithiols", Langmuir, 16: 541-548, 2000.

Sondag-Huethorst, et al., "Potential-Dependent Wetting of Electroactive Ferrocene-Terminated Alkanethiolate Monolayers on Gold", Langmuir, 10: 4380-4387, 1994.

Stole, et al., "In Situ Infrared External Reflection Spectroscopy As A Probe of the Interactions at the Liquid-Solid Interface of Long-Chain Alkanethiol Monolayers at Gold", Langmuir, 6: 1199-1202, 1990.

Takei, et al., "Dynamic Contact Angle Measurement of Temperature-Responsive Surface Properties for Poly(N-Isopropylacrylamide) Grafted Surfaces", Macromolecules, 27: 6163-6166, 1994.

Ulman, Formation and Structure of Self-Assembled Monolayers, Chem. Rev. 96: 1533-1554, 1996.

Weiner, et al., "New Force for Molecular Mechanical Simulation of Nucleic Acids and Proteins", J. Am. Chem. Soc. 106: 765, 1984.

Xia, et al., "Soft Lithography", Angew Chem. 37: 550-575, 1998.

Yang, et al., Preparation and Characterization of Mixed Monolayers of Thiol Analogues of Cholesterol and Fatty Acids, Langmuir, 13: 3210-3218, 1997.

Zamborini, et al., "Corrosion Passivation of Gold By N-Alkanethiol Self-Assembled Monolayers: Effect of Chain Length and End Group", Langmuir, 14: 3279-3286, 1998.

* cited by examiner

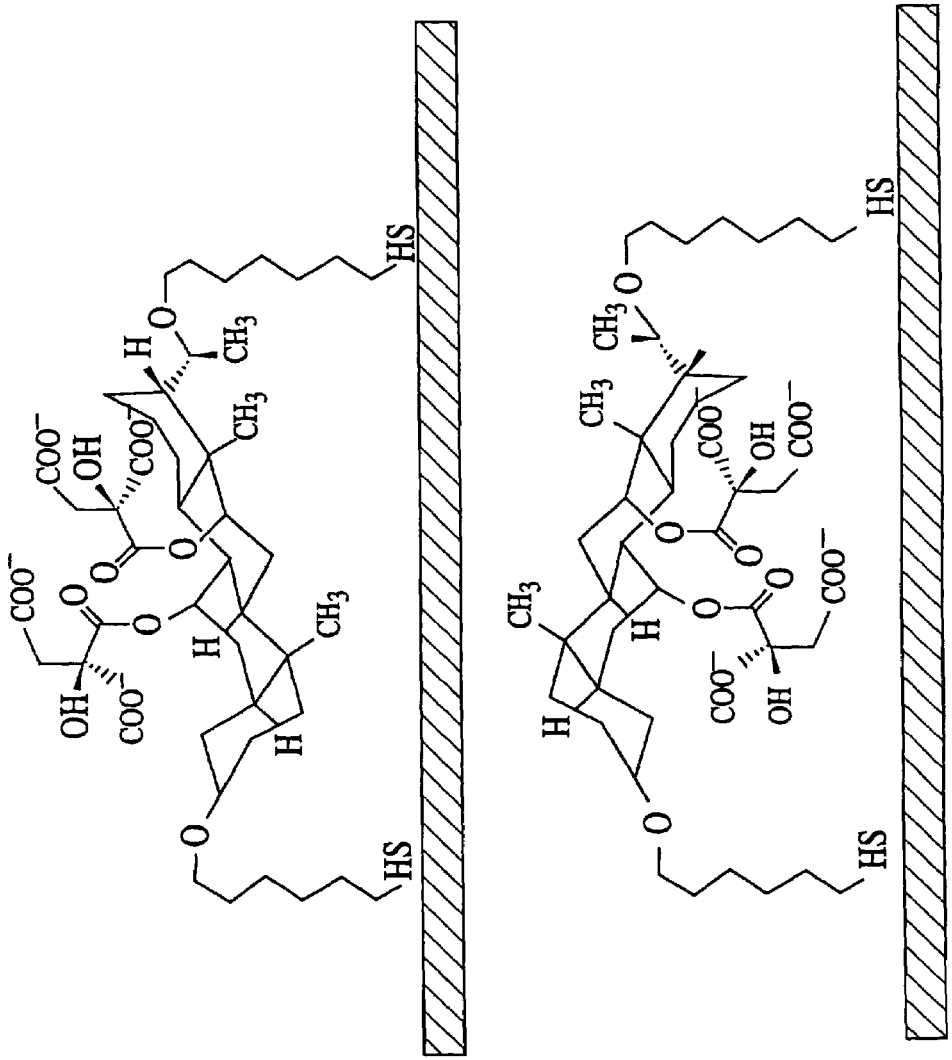

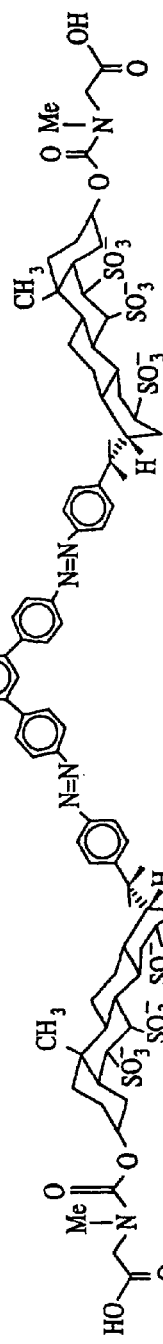
FIG.5A
FIG.5B

SWITCHABLE SURFACES

This application claims priority from and is a divisional of U.S. application Ser. No. 10/284,794, filed Oct. 31, 2002 now U.S. Pat. No. 7,020,355, which claims priority from U.S. Provisional Application No. 60/350,090, filed Nov. 2, 2001, the entire contents of both of which are incorporated herein by reference.

FIELD OF THE INVENTION

This invention pertains to surfaces having properties that may be changed upon application of external stimuli and methods of producing such surfaces.

BACKGROUND OF THE INVENTION

Much work has been done over the last decade on self-assembled monolayers (SAMs) created on substrates like silicon, silicon dioxide, silver, copper or gold. Research on thiol monolayers on gold surfaces has resulted in technologies such as soft lithography. Applications of SAMs include sensor development, corrosion protection and heterogeneous catalysis. SAMs have been used as templates for organic synthesis and layer-by-layer adsorption. Their interaction with cells and proteins is well understood and micro-structured SAMs have been used to manipulate cells. All these techniques are based on a common approach: spontaneous monolayer formation of thiols on gold was used to achieve a densely packed two-dimensional crystal which offers reactive head groups for further modification. Chemisorption of thiols on gold occurs as a self-driven process and the packing of the thiols is mainly determined by geometrical aspects. Therefore, the monolayer is thought to be a closely packed layer with its alkyl chains being tilted relative to the surface at a specific tilt angle. An unmodified alkanethiol monolayer has a tilt angle between 20 and 30°. The distance between single alkyl chains is typically 5 Å (Ulman, Formation and Structure of Self-assembled Monolayers, *Chem. Rev.* 96, 1533-1554, 1996). Due to the spatial limitations and hydrophobic interactions between the alkyl chains, surrounding guest molecules are not expected to migrate into the monolayer. Rather, the head groups are thought to be the frontier line that determines interactions with the surrounding medium. For certain applications in electrode or sensor development, however, a monolayer with an adjustable degree of transparency for small chemical species might be desirable. It is thus desirable to control the density of the monolayer to produce membrane-like structure with a porosity of nanometer-scale is thereby created.

Self-assembled monolayers have been used to control and pattern the properties of a variety of surfaces. However, there is very little research concerning controlled switching between different surface properties. Okano's group reports that the wetability of a surface may be controlled by changing the temperature around the lower critical solution temperature (LCST) of poly(N-isopropylacryl)-grafts (Takei, et al., Dynamic Contact Angle Measurement Of Temperature-Responsive Surface Properties For Poly(N-Isopropylacrylamide) Grafted Surfaces. *Macromolecules* 27, 6163-6166, 1994). Lahann has also reported switching the surface properties of a stable fixed layer bound to a substrate (German Patent Publication 199 05 792, published Aug. 17, 2000). Accordingly, it is desirable to develop a method by which the surface properties of a self-assembled monolayer or similar structure may be reversibly switched upon application or removal of an external force field. The microscopic physico-chemical properties of the surface depend on the molecular structure of the interface of the surface with its environment (DeGennes, Wetting: Statistics And Dynamics. *Rev. Mod. Phys.* 57, 827-863, 1985). Applications such as microfluidic, bioseparation, optical displays, and sensors may benefit from techniques that manipulate the molecular composition of a surface.

Since the wetting behavior of a flat solid substrate is defined by the molecular-level structure of the interface, diverse approaches have been used to control wetting behavior (Mittal, *Polymer Surface Modification: Relevance To Adhesion*, VSP, Utrecht, 1996; De Crevoisier, et al., Switchable Tackiness And Wettability Of A Liquid Crystalline Polymer. *Science* 285, 1246-1249, 1999; Ichimura, et al., Light-Driven Motion Of Liquids On A Photoresponsive Surface. *Science* 288, 1624-1626, 2000; Abbott, et al., Reversible Wettability Of Photoresponsive Pyrimidine-Coated Surfaces. *Langmuir* 15, 8923-8928, 1999; Chaudhury, et al., How To Make Water Run Uphill. *Science* 256, 1539-1541, 1992). Temporal control of wetting properties has been demonstrated by elegant methods based on electrochemical surface modifications (Sondag-Huethorst, et al., Potential-Dependent Wetting Of Electroactive Ferrocene-Terminated Alkanethiolate Monolayers On Gold. *Langmuir* 10, 4380-4387, 1994; Byloos, et al., Phase Transitions Of Alkanethiol Self-Assembled Monolayers At An Electrified Gold Surface. *J. Phys. Chem. B* 105, 5900-5905, 2001; Iannelli, et al., Adsorption Of Pyrazine At The Au(111)/Aqueous Solution Interface. *J. Electroanal. Chem.* 376, 49-57, 1994) such as reversible oxidative desorption of surfactants (Gallardo, et al., Electrochemical Principles For Active Control Of Liquids On Submillimeter Scales. *Science* 283, 57-60, 1999). These systems require chemical reactions in order to control surface wettability. It is desirable to dynamically control surface wettability without relying on chemical reactions.

SUMMARY OF THE INVENTION

In one aspect, the invention is a method of reversibly modifying a property of a surface. The method comprises depositing a nanolayer of a material on a substrate and applying an external stimulus to the substrate. When the stimulus is applied, the nanolayer shifts from a first conformation state to a second conformation state. When the nanolayer is in the first conformation state, the surface is characterized by a first property, and, when the nanolayer is in the second conformation state, the surface is characterized by a second property.

The change in conformation state may include a change from a cis to a trans configured double bond, rotating a molecular group about an axis, opening a hinged molecular group, bending a molecular chain, and unbending a molecular chain. The external stimulus may include application of a voltage, a change in an applied voltage, a change in temperature or pH, exposure to UV light, electromagnetic radiation, or a magnetic field, removal of a magnetic field, a change in capacitance, application or removal of an electrostatic charge, or any combination of the above. Alternatively, or in addition, the external stimulus may comprise exposure to a ligand, biomolecule, small molecule, bioactive agent, ion, or any combination of these. The stimulus may be applied to a portion of the nanolayer, which portion will undergo a change in conformation state.

The nanolayer may include a plurality of molecular assemblies each having at least first and second information carriers. The molecular assembly may further include an active group that interacts with the external stimulus and a tether that changes from a first conformation to a second conformation when the active group interacts with the external stimulus. When the tether has the first conformation, the properties of the surface are substantially determined by the first information carrier, and, when the tether has the second conformation, the properties of the surface are substantially determined by the second information carrier. Either the first information carrier or the second information carrier, or both, may also be one or more of a tether or an active group. Different molecular assemblies having different compositions may be incorporated into a single nanolayer, and the assemblies may be disposed substantially randomly within the nanolayer. Alternatively, the molecular assemblies may be deposited in separate regions by composition, and the external stimulus may be separately applied to the individual regions.

The molecular assembly may include two tethers. For example, the first and second conformation of the molecular assemblies may be related by a 180° rotation. The external stimulus may be applied to a portion of the nanolayer. The method may further comprise depositing a liquid crystal over the nanolayer, wherein a change in the conformation state of the nanolayer causes a change in orientation of the liquid crystal.

In another aspect, the invention is a substrate having a surface with reversably switchable properties. The surface comprises a nanolayer of material characterized in that, when an external stimulus is applied, the nanolayer switches from a first conformation state to a second conformation state.

In another aspect, the invention is a substrate having a surface having at least first and second properties. The first property is defined by a surface property of the substrate, and the second property is defined by a surface property of a nanolayer deposited on the substrate. The surface density of the nanolayer is adapted and constructed such that the interaction with the surface of a chemical entity having a size less than a pre-determined size is determined by the first property, and the interaction with the surface of a chemical entity having size greater than the pre-determined size is defined by the second property.

In another aspect, the invention is a method of reversably modifying a property of a surface. The method comprises depositing a nanolayer of a material on at least a portion of a substrate and applying an external stimulus to the substrate. When the stimulus is applied, the nanolayer shifts from a first absorption affinity to a second absorption affinity. The method may further comprise causing the nanolayer to shift from the second adsorption affinity to the first adsorption affinity. The affinity may be for a surfactant, water, a predetermined analyte, a biomolecule, a small molecule, or a bioactive agent.

BRIEF DESCRIPTION OF THE DRAWING

The invention is described with reference to the several figures of the drawing, in which.

FIG. 3 depicts an exemplary switchable surface based on flipping of a facial amphiphile without (A) and with (B) application of a positive charge to the substrate;

FIG. 5 depicts a switchable surface based on a single amphiphile dimer (A) that opens upon application of a positive charge (B);

DEFINITIONS

Figure 1:
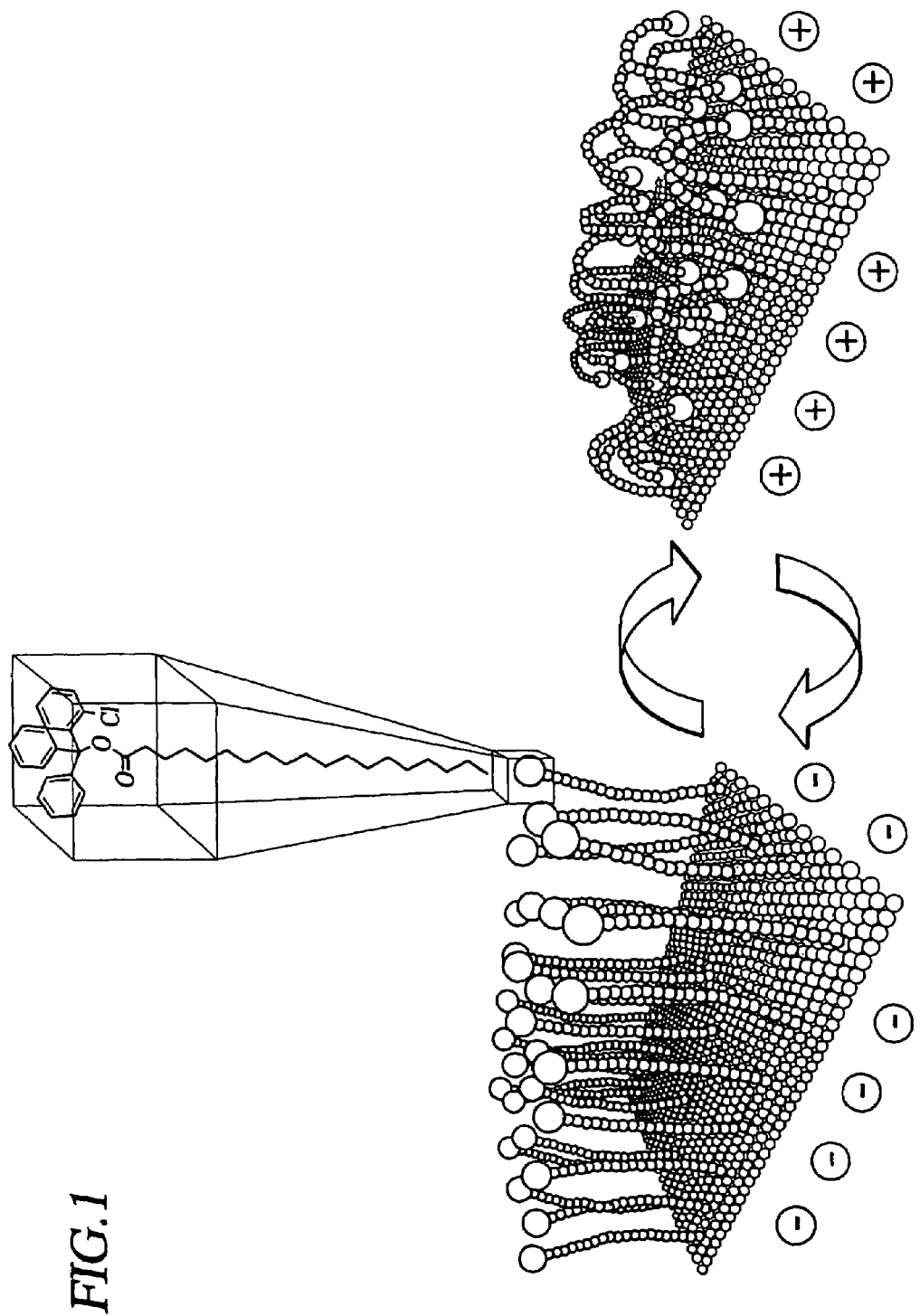
FIG. 1 is an idealistic representation of the transition between the straight-molecule (hydrophilic) and the bent-molecule (hydrophobic) state (ions and solvent molecules are not shown)

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Conformation": The term "conformation", as used herein, describes the arrangement of atoms with respect to one another in a molecule. A change in conformation does not change the sequence of atoms in a molecule but does change their relative positions. Exemplary changes in conformation include a change in the configuration of a double bond from cis to trans, rotation of a single bond about an atom, and a change in the secondary or tertiary structure of a protein.

"Nanolayer": As used herein, a "nanolayer" is a layer of material less than 1 μm thick. In some embodiments a nanolayer may be less than 10 nm thick, less than 5 nm thick, or less than 2 nm thick.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/=dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present invention.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or antithrombotic agents, local anesthetics, ophthalmics, prostaglandins, anti-depressants, anti-psychotic substances, anti-emetics, and imaging agents. In certain embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

DETAILED DESCRIPTION

The invention introduces an entirely different approach for dynamically controlling surface wettability that does not involve chemical reactions, but rather exploits conformational transitions (switching) of molecules confined as a low-density film on a surface (FIG. 1). The films of the invention are based on a dual conformation system and are preferably nanolayers or monolayers. The two conformation states of the nanolayer or monolayer film provide different surface properties to a substrate on which the film is deposited. When a stimulus is applied to the film, the conformation state changes, causing the surface properties to switch. The invention exploits a large number of molecular assemblies to amplify a microscopic effect into a macroscopic surface chemistry. Each molecular assembly includes a tether, an active group, and at least two information carriers. The tether establishes the conformation of the molecular assembly and enables each assembly to achieve a conformation consistent with that of other assemblies in the film. The active group interacts with an external stimulus to change the conformation of the tether and thus the conformation of the molecular assembly. The information carriers determine the surface properties of the substrate for each conformation of the tether. The molecular assembly may also include an anchor that retains the assembly on the substrate. One molecular group may serve more than one role in the molecular assembly. For example, in the single chain molecular assembly depicted in FIG. 1, the chain tethers the assembly to the substrate and also includes the information carrier, a hydrophobic group, for one of the conformations. The charged group at the end of the assembly is the second information carrier and also interacts with the external stimulus, in this case, an electrical charge on the substrate. The thiol group anchors the molecular assembly to the gold substrate.

The surface properties that may be switched using the methods of the invention include any surface property that a skilled artisan wishes to control. FIG. 1 illustrates a change in hydrophobicity or hydrophilicity. Other exemplary properties include electrical charge, chemical composition, polarizability, transparency, conductivity, light absorption, osmotic potential, zeta potential, surface energy, coefficient of friction, and tackiness. The surface properties may also be adjusted to reversibly increase or decrease the affinity of proteins or polynucleotides for the surface. The films of the invention may be used in a variety of media, including liquids, gases, liquid crystals, biological media, solid-solid interfaces, etc.

Practically any substrate, including all classes of materials, e.g., metals, ceramics, glasses, non-crystalline materials, semiconductors, polymers and composites, may be used or adapted for use with the invention. Substrates may also be combined; for example, a substrate of one material may be coated or patterned with a second material. Such coatings may be desirable to provide a specifically tailored set of bulk and surface properties for the substrate. Exemplary deposition techniques for such coatings include chemical vapor deposition (CVD), metal oxide CVD, sputtering, sol-gel techniques, evaporation, pulsed laser deposition, ion beam assisted deposition, and CVD polymerization (Lahann, et al., A New Method toward Micro-Engineered Surfaces Based on Reactive Coating. *Angew. Chem., Int. Ed.* 40, 3166-3169, 2001, German Patent Publication 196 04 173, August, 1997, the entire contents of both of which are incorporated herein by reference). It is not necessary to coat the entire substrate with the second material. The second material may be deposited according to a periodic or other pattern. For example, an electrical circuit may be deposited on the material. The substrates may also be pretreated before deposition of the molecular assemblies. A range of methods are known in the art that can be used to charge, oxidize, or otherwise modify the composition of a surface if desired, including but not limited to plasma processing, corona processing, flame processing, and chemical processing, e.g., etching, micro-contact printing, and chemical modification. Optical methods, such as UV or other high energy electromagnetic radiation or electron beams, may also be employed.

In some embodiments of the invention, it may be desirable to deposit the film on a electrically polarizable surface. Of course, a conductive substrate or coating may be used. Alternatively, a conductive polymer may be used as the substrate or deposited on a surface of the substrate. Exemplary conductive polymers include poly(pyrrole), poly(thiophene), poly(aniline), poly(phenylene vinylene), poly(acetylene), poly(heptadiene), poly(pyridine), or poly(phenylene). Such conductive polymers may be deposited as a stable fixed layer as disclosed in German Patent Publications 199 05 795, published December, 2000, and 199 05 792. Similarly, an electron transfer polymer may be used as a substrate surface. In addition, a non-conductive layer may be deposited on top of a conductive layer. When a voltage is applied to the conductive layer, the non-conductive layer will act as a capacitor, and a static charge will develop on its surface. If the electrical layer is a circuit, then selected portions of a non-conductive layer may be polarized independently. Electroluminescent polymers may also be used to induce a conformation change. Application of a voltage to the polymer will cause it to emit light. The emitted wavelength may be chosen to cause a conformational change in the film.

The films of the invention may be deposited on the surface with a variety of techniques. For example, the any of the deposition techniques described above may be used to form the films of the invention. One skilled in the art will realize that any thin film deposition technique may be used to apply the films of the invention. The films may be easily patterned on a surface using standard photolithographic and soft lithographic techniques, enabling multiple fields containing different molecular assemblies to be deposited. Inkjet printing and automated (robotic) techniques that can precisely deposit small spots of material on a substrate may also be exploited to pattern the surface. In addition, Langmuir Blodgett or layer by layer techniques (see Decher and Hong, *Ber. Bunsenges. Phys. Chem.* 95:1430, 1991 and Decher, *Science*, 277:1232, 1997) may be used to deposit the film.

In an exemplary embodiment, the tether may include an anchor group that facilitates molecular self assembly. Anchor groups form chemical bonds with fimctional groups on the substrate surface to form a self assembled monolayer, or SAM. SAMs having different anchor groups such as silane and thiol may be deposited on a wide variety of substrates, as described in U.S. Pat. No. 5,512,131 to Kumar el al. One skilled in the art will realize that SAMs may be deposited from both the solution and the gas phases onto the substrate. In addition, various soft lithography techniques (e.g., micro-contact printing, microtransfer molding, micromolding in capillaries, replica molding, and microfluidics, described in Xia, et al., Soft Lithography, *Angew. Chem.* 37: 550-575, 1998, the contents of which are incorporated herein by reference), may also be used.

Figure 2A:
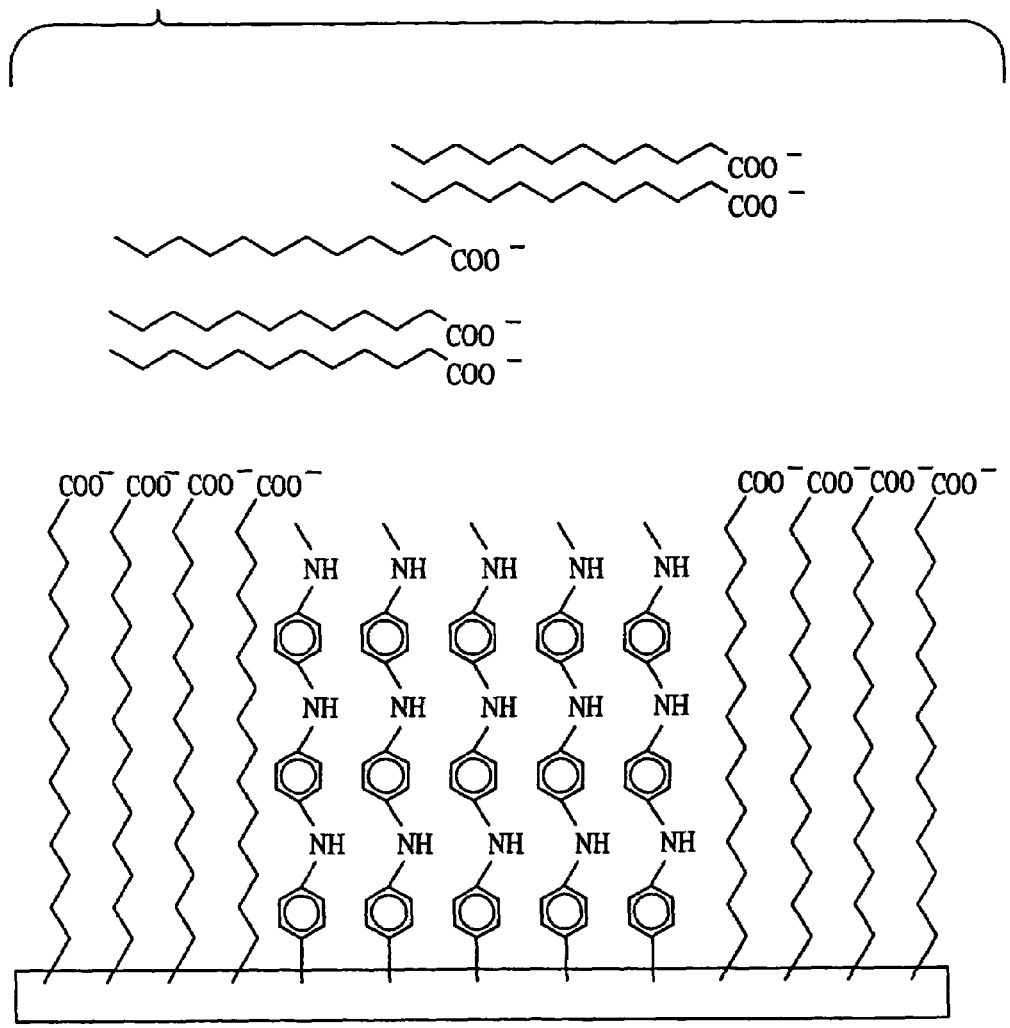
FIG. 2 depicts an exemplary switchable surface based on desorption (A) and adsorption (B) of a surfactant onto a substrate having hydrophilic and switchably conductive areas.
Figure 2B:
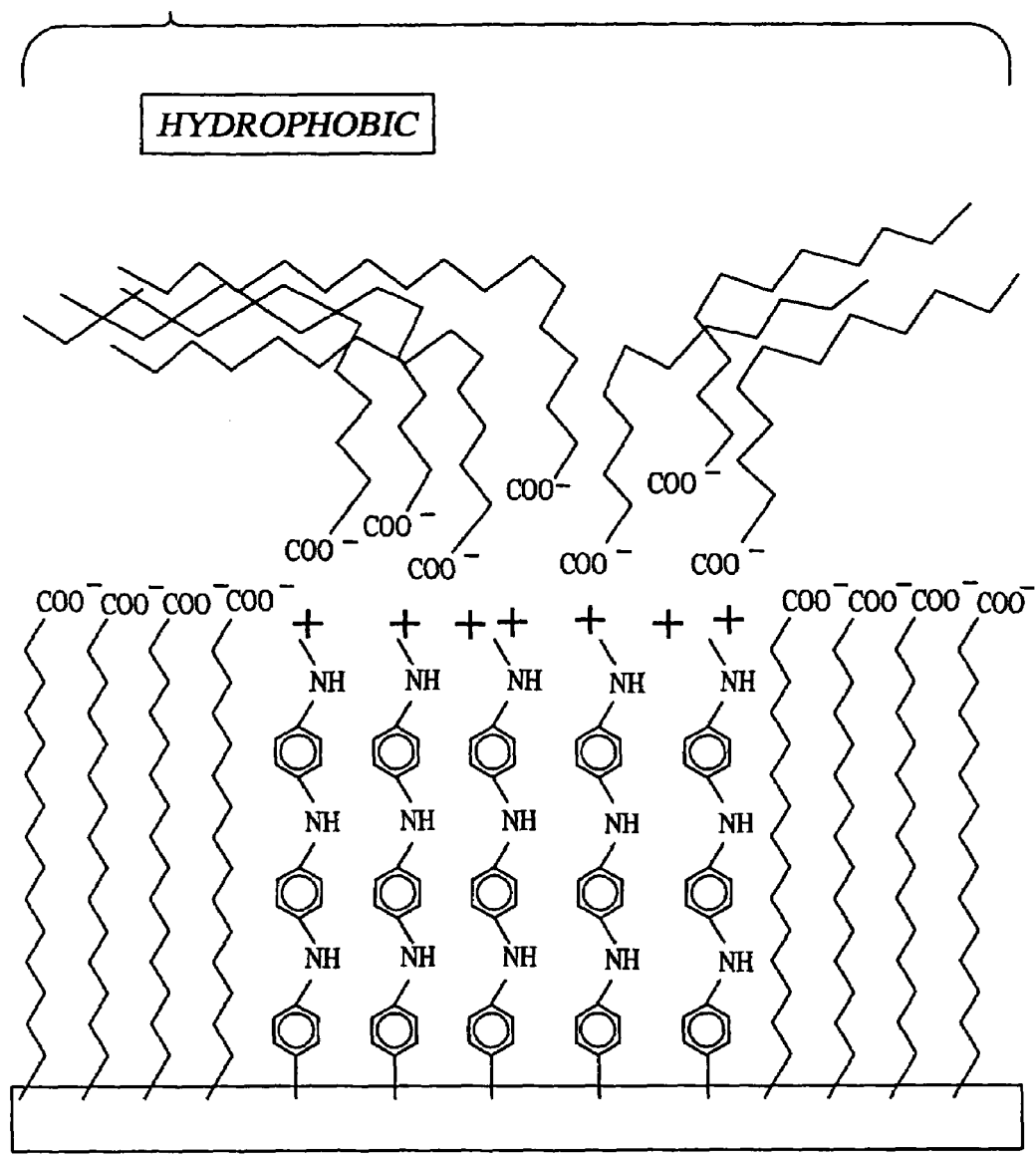

Single chain molecular assemblies may be used in both dense and low-density nanolayers to tailor the surface properties of a substrate. Spontaneous self-assembly allows free energy considerations to determine the distance between individual molecular assemblies. Favorable interactions between tethers, for example, non-covalent interactions, may lead to densely packed SAMs. As discussed below, the assemblies in such monolayers are typically too closely packed to undergo the change in conformation shown in FIG. 1. However, a change in substrate voltage may still enable a change in surface properties. For example, FIG. 2A illustrates a system having a patterned SAM deposited on a substrate. The SAM includes long chain hydrocarbons with terminal carboxylic acid groups interspersed with short oligomers of aniline. When the substrate is neutral, the electron density of the aniline oligomer is evenly distributed among the amine groups and the phenyl groups to render the polymer neutral. When a positive charge is applied to the substrate (FIG. 2B), the electron density shifts such that the amine groups are positively charged. The amine groups interact electrostatically with carboxylate groups on a surfactant dissolved in the surrounding medium. If the carboxylate groups are protonated, they may interact with the amine groups through hydrogen bonds. The long chains on the surfactant molecules interact with each other via van der Waals and other hydrophobic interactions and tend to lay flat over the surface of the remaining SAM rather than extending out into the medium, thus blocking access to the carboxyl groups on the SAM and rendering the surface hydrophobic. This method, of course, depends on the presence of solubilized surfactant molecules in these surrounding medium. The concentration of such molecules in the medium must be high enough to provide good coverage for the surface. In addition, the chain length should be optimized for the relative sizes of the carboxyl-terminated and poly(aniline) portions of the surface. This system has three information carriers—the tethered carbonyl-terminated assemblies, the solubilized surfactant, and the aniline oligomers, which also serve as an active group.

Low density nanolayers of single chain molecular assemblies may be produced by temporarily attaching a bulky endgroup to the assembly, as shown in FIG. 1. The Cl-triphenyl ester group increases the effective size of the assembly, causing the SAM to form with a larger inter-assembly spacing. The triphenylmethyl group is easily hydrolyzed to leave a low-density carboxyl terminated SAM. Other bulky molecular groups, such as tert-butyl and isopropyl, may be used as well. Endgroups used with the invention should be easily cleavable from the molecular assembly without affecting the chemical and mechanical stability of the monolayer. The size for the endgroup will be defined in part by the application for the molecular assembly. For example, different active groups may require different areas for energetically favorable conformational changes (see below). Chromatographic and sensor applications may have different optimal monolayer densities than applications exploiting the switching properties of the surface. Alternatively, the chemistry of the triphenylmethyl group may be modified for use with different assemblies. For example, triphenylacetic acid may be temporarily attached to an amine-terminated chain to form a low-density positively charged monolayer. When at least one of the information carriers in the assembly, preferably a carrier at the end of the chain, includes an electron rich group or an atom that has free electron pairs in its neutral state, one skilled in the art may easily temporarily attach a bulky molecular group to the reactive information carrier to manipulate the density of the monolayer. Exemplary chemistries and molecular groups, are described in March, *Advanced Organic Chemistry*. Fifth edition, John Wiley & Sons, Inc., New York, 1995, the entire contents of which are incorporated by reference herein. In one embodiment, protecting groups may be attached to the assembly. Exemplary protecting groups include fluorenylmethoxycarbonyl (FMOC), t-butyloxycarbonyl (BOC), trisisopropylsilylmethyl, trityl, 2-chlorotrityl, 4-methyltrityl, 4-methoxytrityl, 4,4'-dimethoxybenzylhydryl, adamentyloxy, xantyl, 4-methoxy-2,3,6-trimethyl-benzensulfonyl, and 2,2,4,6,7-pentamethyl-dihydrobenzofurane-5-sulfonyl. Additional protecting groups may be found in Greene, et al., *Protective Groups in Organic Synthesis*. 3$^{rd}$ Edition, Wiley Interscience, New York, 1999, the entire contents of which are incorporated herein by reference.

Alternative methods besides bulky endgroups may be used to control the density of a nanolayer on the substrate surface. For example, two different molecules, a long chain molecule and a short bulky molecule may be codeposited in a single monolayer or nanolayer. Deposition of mixed SAMs is described in Yang, et al., Preparation and Characterization of Mixed Monolayers of Thiol Analogues of Cholesterol and Fatty Acids, *Langmuir*, 13, 3210-3218, 1997 and Shon, et al., Low Density Self-assembled Monolayers on Gold Derived from Chelating 2-Monoalkylpropane-1,3-dithiol, *Langmuir*, 16, 541-548, 2000. The concentration of the two molecules may be adjusted to control their relative density in the nanolayer (and the distance between the long chain molecules). Preferably, the long chain molecule is relatively dilute with respect to the short chain molecule. As a result, the spacing between the long chain molecules will be narrowly distributed about the average. The chain length and molecular size of the short molecule should be optimized to maintain access to the surface for the active group. Preferably, the short molecule includes a bulky group such as phenyl, tert-butyl, triphenylmethyl, isopropyl, or the protecting groups described above.

Codeposition may also be used to switch the properties of the surface between two states that are chemically similar. For example, molecular assemblies with a charged active group and molecular assemblies with a polar information carrier but that may lack an active group (or whose active group reacts to some other stimulus) may be disposed in a nanolayer. When the charged active groups are directed away from the substrate, the surface is hydrophilic. When the active groups are attracted toward the substrate, the surface is still hydrophilic because of the polar molecular assemblies, but the hidden active groups reduces the hydrophilicity of the surface. If the assembly with a polar information carrier changes conformation in response to UV light, then the surface can achieve a third state. A fourth conformation is achieved when both the first (charged) and second (polar) molecular assemblies change their conformations.

In a preferred embodiment, straight chain tethers that are used with the invention have between 5 and 30 carbons. The carbon chains should be long enough to bend over, but not so long that solvent interactions with either the active group or the tether dominate the energetic considerations leading to a transition between the extended and bent conformations. However, it is not necessary that the chain be a hydrocarbon. A polar or other fumctional group may be disposed in the middle of the chain. This group may serve as an information carrier and enable the surface chemistry to switch to other properties besides hydrophobic when the chain bends over. Alternatively, rigid chemical groups such as double and triple bonds, aromatic, polyaromatic, polycyclic, and fused aromatic groups may be incorporated into the tether. These groups will stiffen the molecular assembly in the upright conformation and help dictate the conformation of the assembly when it bends.

In other embodiments, it may be desirable to fabricate a nanolayer that is more geometrically stable with respect to both chemical and physical environmental influences. Thus, a nanolayer with a more rigid tether than the long chain hydrocarbons described above might be used. For example, a molecule that is tethered at both ends to the surface would be very stable with respect to environmental influences. If a tethered molecule has a hydrophobic side and a hydrophilic side and is derivatized with an active group on one side, then applying a charge or voltage to the surface will cause the molecule to flip 180° and expose its opposite side to the medium. FIG. 3A shows a molecule of cholic acid derivatized with two alkylthiol chains via an ether linkage and with carboxylate groups via ester linkages to form a facial amphiphile. When a positive charge is applied to the surface, the molecule flips over to place the carboxylate groups in closer proximity to the positively charged surface, exposing the methyl groups on the other side of the molecule to be surrounding environment (FIG. 3B). Other two faced molecules include cyclophanes and crown ethers, which may be derivatized to prepare two sides having different properties using methods well known to those skilled in the art (Lehn, et al., *Comprehensive Supramolecular Chemistry: Molecular Recognition: Receptors of Molecular Guests*, Vol 2, Pergamon Press, 1996, the contents of which are incorporated herein by reference). If molecular self-assembly is employed to deposit assemblies such as that depicted in FIG. 3, the assemblies are preferably allowed to form as dense a monolayer as is energetically favorable.

A synthesis pathway has been developed for obtaining facial amphiphilies. 3α, 7α, 12α-Trihydroxy-5β-cholan-24-oic acid (cholic acid) was used as starting material for the developing of structures with facial amphiphily. The structure of cholic acid is

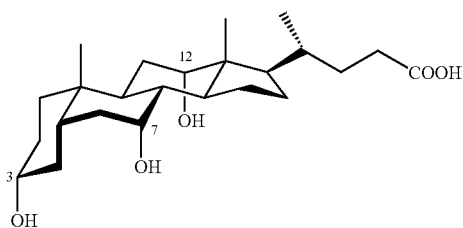

Esterification of cholic acid and subsequent reduction of the carboxyl group yielded 5β-cholane-3α, 7α, 12α, 24-tetraol. A protection strategy must then be established to discriminate between lateral and horizontal alcohol groups. This technique was used to synthesize 3α-hydroxy-7α, 12α-bistrifluoroacetate-5β-cholan-24-ol, a molecule that is characterized by protection groups in position 7 and 12. Various ways can be explored to introduce thiol groups in positions 3 and 24 and are based on procedures known to a person skilled in the art. These thiol groups are necessary when self-assembly on gold surfaces is intended. Subsequent deprotection of the protected hydroxy groups in positions 7 and 12 delivered a molecule that is ready for introduction of charged moieties on the topside of the plane build by the polycyclic framework. Several methods, such as acetyl chloride route, carbodiimide route, or active ester route can be explored for modification along with various reactants such as N-protected amino acids, citric acid, citric acid esters.

Figure 4A:
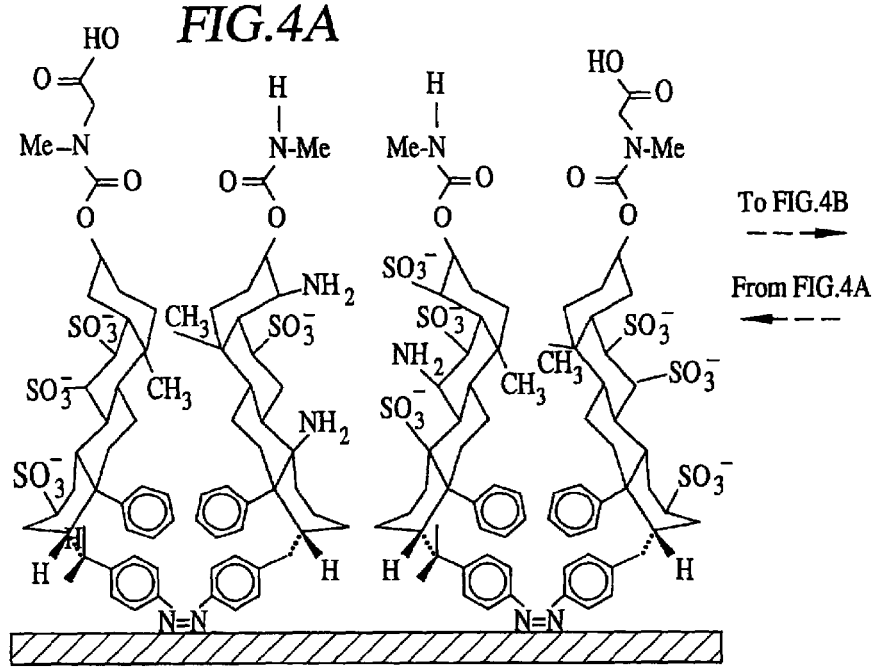
FIG. 4 depicts an exemplary switchable surface based on a pair of dimeric amphiphiles (A) that do not unfold under application of a positive charge (B)
FIG. 4C depicts the unfolding of the switchable surface of FIG. 4A upon exposure to UV light.
Figure 4B:
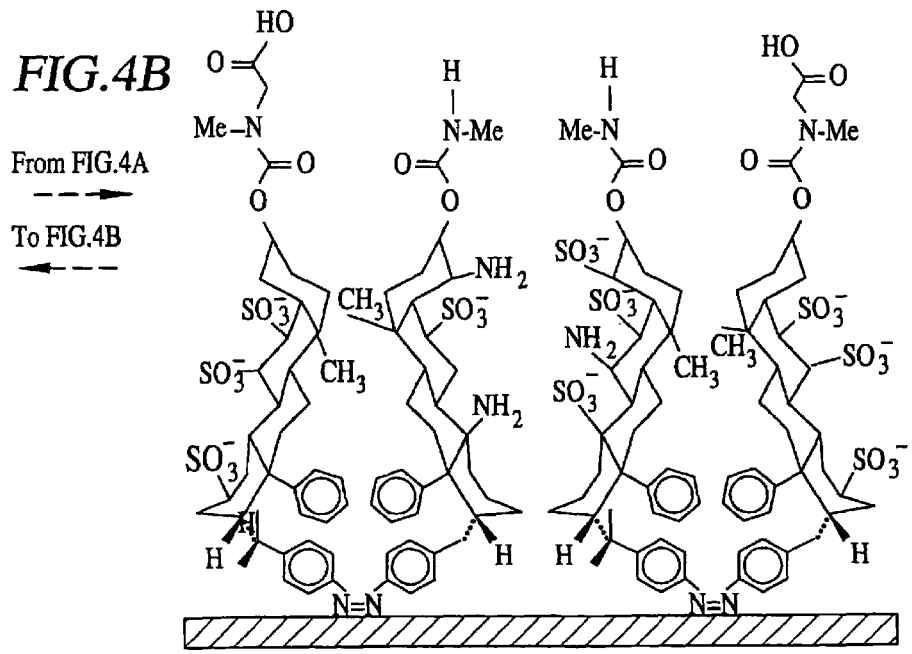
Figure 4C:
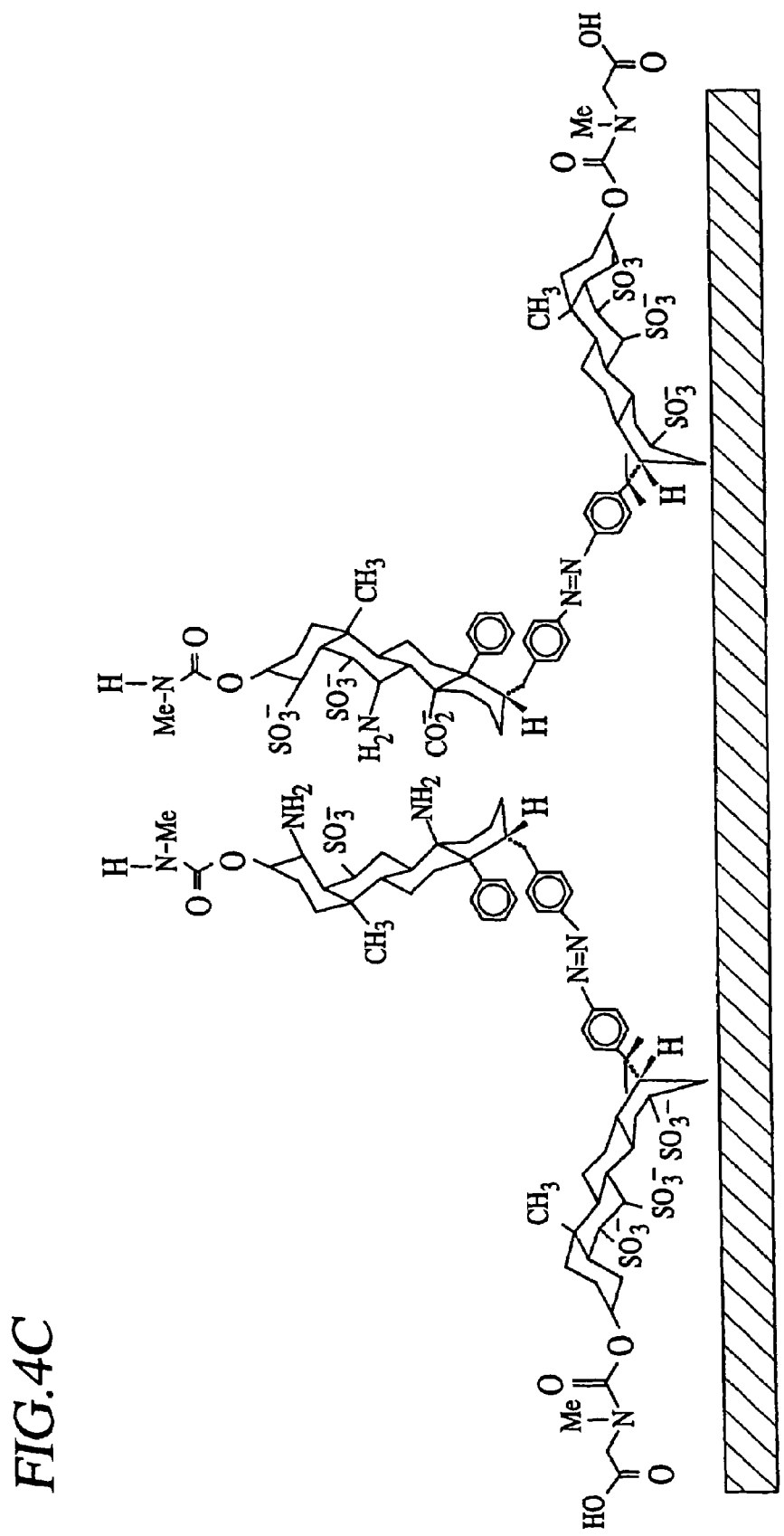
Figure 6A:
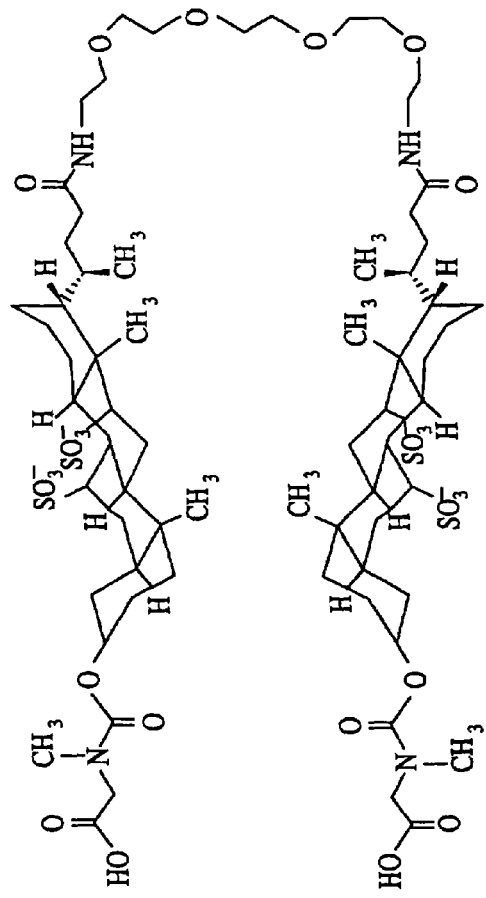
FIG. 6 depicts an embodiment of the invention in which a modified cholic acid dimer (A) is employed to provide a hydrophilic and a hydrophobic surface upon application of a negative or a positive charge, respectively (B)
Figure 6B:
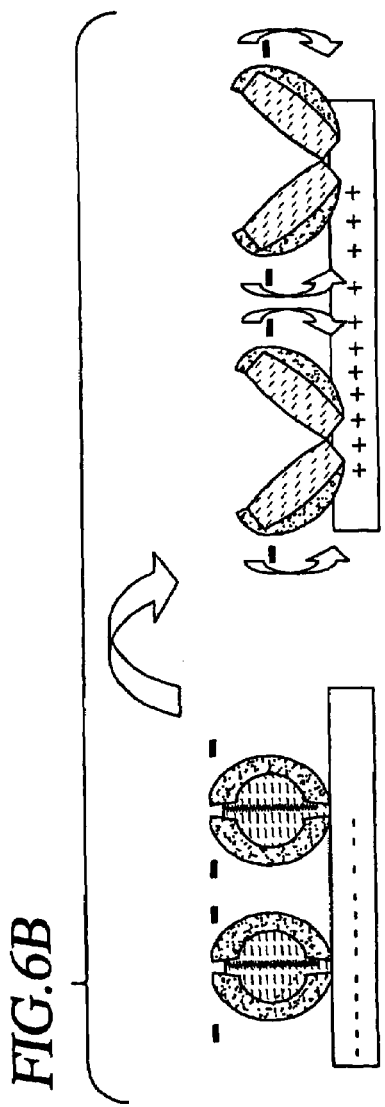

Other amphiphiles may also be utilized to create switchable surfaces according to the invention. FIG. 4A exhibits two amphiphilic "dimers" (the two arms are not idenical) in a folded, closed configuration connected via an azo linkage. Starting from a tri-protected cholic acid pentafluorophenol ester, a dimer can be synthesized by reaction with mercapto pyrimidine. Alternatively, starting material 3α, 7α, 12α tris-trifluoroacetate-5β-cholan-24-ol can be selectively protected in positions 3, 7, and 12 and then reacted with bivalent spacers such as diisocyantes. Both pathways result in suitable assemblies. The inner arms of the two dimers are attracted to each other via electrostatic interactions between the sulphate and amine groups. The dimers are held closed via hydrophobic interactions between the methyl groups and pi-orbital interactions between the phenyl groups. Even if the substrate is positively charged, the strength of the interactions between the dimers is sufficient to keep them closed (FIG. 4B). Exposure of the system to UV light enables a change in conformation of the azo groups from cis to trans (FIG. 4C). The two dimers unfold and are then held open by electrostatic interactions between the sulphate groups and the surface. Application of a negative charge to the surface enables the dimer to refold on itself (FIG. 4B). FIG. 5A illustrates a second dimer that, in its closed form, forms a cup having a hydrophobic interior and a negatively charged exterior. Application of a positive charge to the substrate causes the cup to open, rendering the surface hydrophobic as the methyl, phenyl, and cyclohexane groups are exposed to the surrounding environment (FIG. 5B). FIG. 6A illustrates a cholic acid dimer whose hydroxyl groups have been replaced with charged sulfate groups. As shown in FIG. 6B, application of a positive charge to the substrate causes the dimer to unfold and expose its hydrophobic interior to the surrounding environment. Reversal of the substrate charge polarization repels the negatively charged sulfate groups and recloses the dimer.

Such folding amphiphiles may be deposited on a substrate as Langmuir-Blodgett films or via the deposition techniques described above. The electrostatic repulsion between the solely negatively charged faces will help space the molecules on the surface. If the repulsion does not provide sufficient spacing to allow the dimers to fully unfold, bulky counterions may be used to increase the spacing. Alternatively, the dimers may be deposited on the surface in the open conformation.

Several techniques may be used to switch the properties of the assembly. For example, an assembly with a charged active group will exhibit one conformation when the substrate is neutral and a second conformation when a voltage is applied to the substrate, as shown in FIG. 1. If a non-conductive substrate is used, the substrate may be charged by applying a charge across the substrate and allowing it to charge as if it were a capacitor. A charged or polar active group will still be able to interact with the substrate via electrostatic interactions, and discharge of the capacitor will release the active group and permit a change in conformation. Dipolar active groups such as

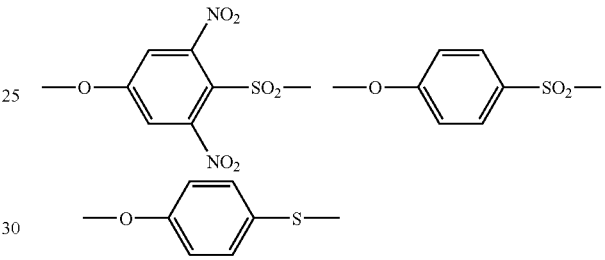

may also be used with the invention. Electrical charge or polarization will also change the conformation of an alpha helix, especially of a protein, which will adjust its conformation (e.g., to a coil) to place different amino acids close to the substrate surface. Alternatively, if the chain undergoes a conformational change in the presence of UV light, then the surface may be switched without the application of any charge at all or with the combination of applied charge and light, as discussed above in connection with FIGS. 4 and 5. Magnetic particles, atoms, or ions may be incorporated into the molecules which will be attracted to the surface on a magnetic field is applied. Diamagnetic and paramagnetic atoms and ions may easily be chelated with organic molecules that can be deposited as nanolayers and used with the invention. In addition, nanosized magnetic particles may be coated with a surfactant that provides the desired surface property, enabling the particle to act both as an active group and an information carrier. Stable organic radicals such as TEMPO (2,2,6,6-tetramethyl-1-piperidinyloxy free radical) will also interact with a magnetic field. Alternatively, changes of pH may be used to protonate or deprotonate terminal active groups and modify their charge relative to a charged substrate. Temperature may also be used to modify the conformation of the molecular assembly. For example, an alpha helix (e.g., of a biomolecule) may exhibit a conformational change at a given temperature, or a magnetic particle may be released from the surface above its Curie temperature. In a layer by layer nanolayer comprising materials that can change their charge or some other property in response to an external stimulus, application of the stimulus may switch the alternating charges of the film (e.g., from +−+− . . . to −+−+ . . . ) or cause a change (e.g., conformational, chemical, electronic or magnetic) in the uppermost layer or the entire film.

When the external stimulus is applied and the conformation state of the nanolayer is changed from a first to a second state, a sufficient number of tethers should change their conformation to change the surface properties of the substrate. At least 60%, preferably 75%, and more preferably 90%, of the tethers should change their conformation in response to an external stimulus. The change in conformation state is preferably reversible. The change in conformation state may be effected by removing or reversing the external stimulus, depending on the surface property. After reversing the conformation state of the nanolayer, at least 60%, preferably 75%, and more preferably 90% of the tethers should have the original conformation.

Practically any molecular group may be used as an information carrier. The two information carriers preferably have different properties. FIG. 1 depicts a molecular assembly with a charged information carrier and a hydrophobic information carrier. Information carriers may be polar or aromatic as well and may be either positively or negatively charged. Magnetic particles, atoms, or ions used as active groups may also serve as information carriers. The wide variety of surface properties that may be provided by the nanolayers of the invention may be optimized by selecting appropriate molecular groups and forming them into molecular assemblies using standard synthetic chemcial techniques (March, 1995).

One advantage of the surfaces of the invention is that their switchability is largely solution independent. Even for the dense films depicted in FIG. 2, the surface charge changes when a voltage is applied—adsorption of the surfactant provides a further change, from a surface with positive and negative charges to a hydrophobic surface. The conformational change in response to electrical charge or exposure to UV light results from an interaction between the stimulus and the active group. For example, while a solution with a high ionic strength may compete with a charged substrate for the active group, the voltage applied to the substrate may be selected to overcome any interaction with the surrounding medium.

The nanolayers of the invention enable the magnification of a molecular level event. Nanolayers of molecular assemblies designed to switch together in response to a stimulus amplify the chemical effects of the individual assemblies to change a macroscopic surface property. This effect can also be extended into a third dimension. For example, the nanolayers can be constructed to facilitate adhesion of cells and biomolecules in one conformation and to repel the adhered material or to change the organization of deposited biomolecules in a second conformation. Liquid crystals can also be manipulated using the techniques of the invention (see below).

Development of a Low Density Monolayer

Alkanethiols adsorbed on gold form highly oriented assemblies that may be a potential platform for the design of switchable surfaces. However, all in situ evidence so far indicates that applied electrical potentials have no effect on long chain alkanethiol monolayers on gold in aqueous electrolytes within the range of chemical stability (Hines, et al., Conformation Of Alkanethiols On Au, Ag(111), And Pt(111) Electrodes: A Vibrational Spectroscopy Study. *Langmuir* 11, 493-497, 1995). In one embodiment, our approach utilizes a low-density self-assembled monolayer (SAM) of 16-mercaptohexadecanoic acid on gold (111) synthesized from a novel precursor (FIG. 1). The precursor is designed to assemble into a well-defined monolayer that, on demand, can be transformed in a low-density assembly. This design is chosen to ensure sufficient free volume for switching and may allow molecular reorientations to be controlled, e.g. by application of a weak electric potential. Preferential exposure of either hydrophilic or hydrophobic moieties to the surrounding medium will then result in switching of macroscopic surface properties such as wettability. In contrast, spontaneous self-assembly of 16-mercaptohexadecanoic acid on gold yields a high-density, crystalline SAM, in which sulfur atoms are hexagonally packed with a S—S spacing of 4.99 Å (Chidsey, et al., Chemical Functionality In Self-Assembled Monolayers: Structural And Electrochemical Properties. *Langmuir* 6, 682-691, 1990). The dense package and the strong hydrophobic interactions in this SAM restrict dynamic molecular motions to the outermost atoms (Schoenfisch, et al., Effects Of Electrolyte And Potential On The In Situ Structure Of Alkanethiol Self-Assembled Monolayers On Silver. *Langmuir* 15, 509-517, 1999; Anderson, et al., Effects Of Applied Potential Upon The In Situ Structure Of Self-Assembled Monolayers On Gold Electrodes. *Langmuir* 10, 1638-1641, 1994) and prevent it from switching.

Figure 7:
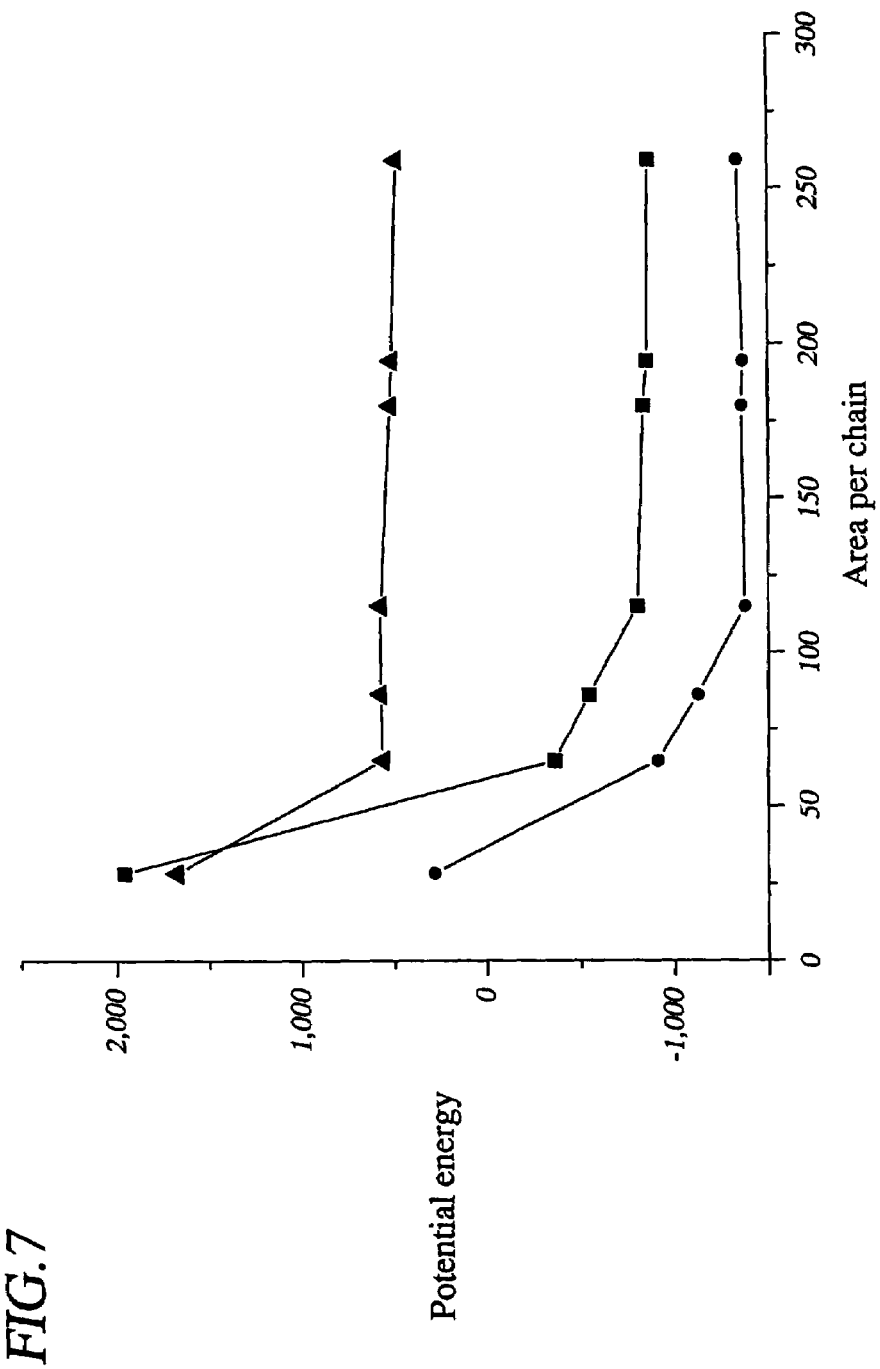
FIG. 7 is a graph showing internal energy (square), van der Waals contributions (dot), and energy contributions due to steric interactions (triangle) of SAMs as a function of area per bent alkanethiol molecule.

The precursor molecule was designed by first identifying the optimum alkanethiol density for switching. Using molecular simulations, we searched for the energetically favorable S-S spacing that will permit conformational reorientations of the molecules (FIG. 7). Structural properties of SAMs were investigated using (NVT) molecular dynamics simulations following the Verlet algorithm implemented into Molecular Operating Environment (MOE, CCG). A SAM was created based on 64 alkanethiol molecules with a nearest neighbor distance between 5.77 and 17.30 Å confined on a hexagonal gold lattice (Au—Au distance of 2.88 Å). Periodic boundary conditions were enforced in the plane of the monolayer and sulfur and gold atoms were fixed in space. The intermolecular potential was adopted from literature (Cornell, et al., A Second Generation Force Field For The Simulation Of Protein, Nucleic Acids, And Organic Molecules. *J. Am. Chem. Soc.* 117, 5179-5197, 1995; Weiner, et al., New Force Field For Molecular Mechanical Simulation Of Nucleic Acids And Proteins. *J. Am. Chem. Soc.* 106, 765, 1984) and the potential describing the interactions between carbon and sulfur atoms with the gold surface was selected to mimic the values reported by Hautman and Klein (Hautman, et al., Simulation Of A Monolayer Of Alkyl Thiol Chains. *J. Chem. Phys.* 91, 4995-5001, 1989). In attempting to discriminate a SAM with optimum steric conditions for bending, we did not consider electrostatic contributions, or interactions with solvent molecules. The cutoff for the non-bonded parameters was 6.5 to 7 Å; a smoothing function was applied for this range. MD simulations were conducted at 300 K for 0.5 ns with energy-minimized SAMs using a time step of 5 fs. The subsequent energy minimization (Truncated Newton) was deemed achieved either if RMS values below 0.01 were reached or if the distance between sulfur and carbonyl carbon exceeded 4 Å.

Since alkanethiolates adsorbed on Au(111) build either a hexagonal ($\sqrt{3}\times\sqrt{3}$)R30 or a c(4×2) superlattice, only certain combinations of area-per-molecule values permit effective packing (Li, et al., Relationship Between Packing Structure And Headgroups Of Self-Assembled Monolayers On Au(111): Bridging Experimental Observations Through Computer Simulations, *J. Phys. Chem. B* 102, 2935-2946, 1998). For SAMs with area-per-molecule values in the range between 28.8 and 259.1 $Å^2$, the potential energy was determined (FIG. 7, square), and reasonable low potential energies were found for area-per-molecule values of 64.80 $Å^2$ or higher (compared to 21.6 $Å^2$ in a regular SAM). Denser packed SAMs are characterized by strong repulsive interactions. These sterically motivated contributions (triangle)

account for most of the high internal energy of a SAM with an area-per-molecule of 28.8 Å$^2$, decline then fast and reach a plateau for higher area-per-molecule values. The van der Waals energy (dot) passes a minimum at 64.80 Å$^2$, where repulsive contributions are already minimal while dispersive interactions have still a significant impact. As the area-per-molecule further increases, the van der Waals interactions between carbon atoms diminish and the weak carbon-gold interactions become dominant.

Keeping these energetic considerations in mind, the precursor molecule, 16-mercaptohexadecanoic acid Cl-triphenyl ester (FIG. 1) was synthesized. Its molecular dimension defined by a space-filling end group (67.56 Å$^2$) matches closely with the area of 64.80 Å$^2$ that permits establishment of a low-energy SAM of bent molecules. Prior to esterification, selective protection of the thiol group was achieved by converting carefully purified 16-mercaptohexadecanoic acid (5 mmol, Aldrich), dimethoxitrityl chloride (Aldrich), and triethylamine (6 mmol, Aldrich) in a mixture of tetrahydrofuran, acetic acid and water (5:4:1) for 14 h at room temperature under an argon atmosphere. After removal of the solvent under reduced pressure, the remaining residue was dissolved in ethyl ether. Extraction with ammonium bicarbonate (1 M) delivered crude S-protected acid that was purified by column chromatography (silica, hexane/ethyl acetate/methylene chloride (6:2:1)). Subsequently, the S-protected acid (4 mmol) was allowed to react with chlorotrityl chloride (5 mmol, Novabiochem) and diisopropylethylamine (9 mmol, Aldrich) in methylene chloride for 14 h at room temperature to yield the S-protected ester (purification as described for S-protected acid). For deprotection of the thiol group, the S-protected ester (1 mmol) was dissolved in 20 ml of tetrahydrofuran and methanol (3:1) and 2 ml of an aqueous solution of sodium acetate (3 M). Silver nitrate (2 mmol) dissolved in a mixture of water and methanol (1:5) was added and the resulting suspension was stirred at room temperature for 1 hour. Subsequent centrifugation and re-suspension in 20 ml of the tetrahydrofuran/methanol mixture delivered a crude intermediate that was subsequently converted with dithioerythritol (2 mmol, Aldrich) in aqueous sodium acetate (3 M) for 5 h. The precipitate was filtered, and the remaining filtrate was concentrated under reduced pressure. Extraction with ethyl acetate and subsequent column chromatography (silica, ethyl acetate/hexane (2:5)) yielded Cl-triphenyl methyl ester. Only freshly prepared precursor was used for SAM formation.

The low-density SAM was prepared by simply immersing a gold (111) substrate in a solution of the precursor in ethanol. The SAM was formed by immersing a previously annealed gold substrate (root-mean square (RMS) roughness acc. to AFM<4 Å) into a solution of the Cl-triphenyl methyl ester (1 mM, ethanol) for 16 h. The thickness of this SAM as examined by ellipsometry was 20.52 (±1.37) Å. Subsequently, the ester group was cleaved by treatment with trifluoroacetic acid vapor at 37° C. for 1 h. Complete deprotection was verified by the absence of the XPS signal of chlorine (Axis Ultra X-ray, Kratos Analytical). In addition, the characteristic IR signals of the Cl-triphenyl ester group were no longer observed (all IR spectra recorded under a grazing angle of 82°, BioRad FTS 70). The carboxylic acid group was then deprotonated by incubation with an aqueous Cesium hydroxide solution (0.3 M) and completeness was monitored by IR spectroscopy. Formation of the well-defined SAM was verified by Infrared (IR) and X-ray photoelectron spectroscopy (XPS).

In air, the assembly collapsed into a disordered configuration with a thickness of 10.90 (±0.89) Å as confirmed by ellipsometry. This value is significantly lower than the thickness of a dense SAM (20.35±0.99 Å). The collapsed structure was also demonstrated by infrared spectroscopy, which revealed general features of a disordered monolayer, e.g. the typical red-shift of the methylene bands to 2929 and 2858 cm$^{-1}$. Furthermore, C=O stretching vibrations at 1736 and 1716 cm$^{-1}$ of the switchable SAM prior to deprotonation prove coexistence of isolated and face-to-face oriented carboxylic acid groups. This is characteristic for a structure with end groups partially embedded inside the SAM (Nuzzo, et al., Fundamental Studies Of Microscopic Wetting On Organic Surfaces. 1. Formation And Structural Characterization Of A Self-Consistent Series Of Polyfunctional Organic Monolayers. *J. Am. Chem. Soc.* 112, 558-569, 1990) and is also supported by the increased static contact angle with water of 62° as compared to 10° measured for the dense SAM. The less densely packed monolayers showed excellent stability and remained unaltered after exposure to ambient conditions for four weeks (confirmed by XPS and IR spectroscopy). Similar to our results, Zamborini and Crooks pointed out the stability of defect SAMs, as they did not show decreased protection properties in their study (Zamborini, et al., Corrosion Passivation Of Gold By N-Alkanethiol Self-Assembled Monolayers: Effect Of Chain Length And End Group. *Langmuir* 14, 3279-3286, 1998). We then concluded that a chemically stable, low-density SAM was formed.

Prior to examining whether this low-density SAM reorients in response to electric potentials, we confirmed conformational freedom of alkanethiolates by studying their response to changes in the chemical environment of the assembly. Sum-frequency generation spectroscopy (SFG) was used for this purpose since it exploits a highly surface-sensitive nonlinear optical process (Shen, Surface Properties Probed By Second-Harmonic And Sum-Frequency Generation. *Nature* 337, 519-525, 1989). To generate the SFG spectra, tunable mid-infrared light (1400-4000 cm$^{-1}$) was generated by difference frequency mixing tunable near-infrared light with the fundamental beam of the Nd:YAG pump laser in a LiNbO$_3$ or AgGaS$_2$ crystal. The near-infrared light is produced through optical parametric generation and amplification of 532 nm light in angle tuned barium borate crystals. The infrared and visible beams were incident on the liquid/solid interface at 40° and 35° and had energy densities of 4 mJ/cm$^2$ and 15 mJ/cm$^2$, respectively. SFG spectra are an average of 10 scans with 5 cm$^{-1}$ resolution. SFG signal was collected for 1 to 5 seconds at every 5 cm$^{-1}$ interval. SFG data have been normalized with respect to the reflected IR beam from the electrode to ensure that no false SFG peaks were observed due to strong IR absorption by the thin film of electrolyte above the electrode surface. The lines in the SFG spectra are drawn as a guide to the eye.

Figure 8:
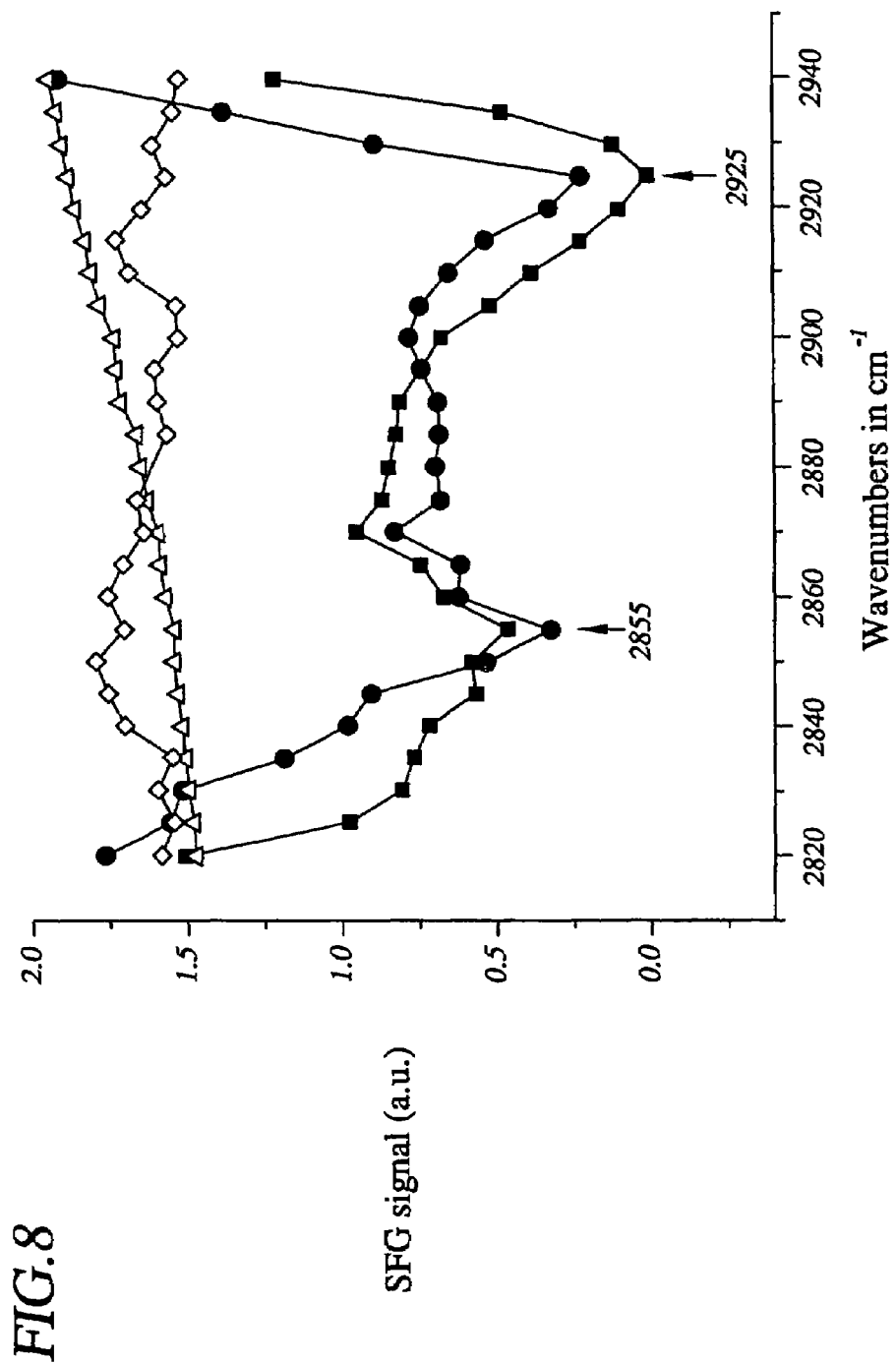
FIG. 8 shows the in situ SFG spectra of the CH-stretch region (2820-2940 $cm^{-1}$) for the switchable SAM during exposure to air (square), $d^3$-acetonitrile (triangle), $d^2$-water (diamond) and $d^8$-toluene (circle)

The intensity of a peak in the SFG spectrum is affected by the orientation of the adsorbed molecules. An ordered monolayer of all-trans oriented molecules is locally centrosymmetric and hence, by rule of mutual exclusion, its CH$_2$-modes are sum-frequency inactive. Gauche conformations break the local symmetry and give rise to SFG-signals of the CH$_2$-groups (Ong, et al., Sum-Frequency Spectroscopy Of Monolayers Of Alkoxy-Terminated Alkanethiols In Contact With Liquids. *Langmuir* 9, 1836-1845, 1993). When exposed to an apolar environment such as air or toluene, the molecules were found to be in a disordered conformation. This state was rich in gauche-conformations resulting in SFG-signals of the CH$_2$-groups at wavelengths of 2925 and 2855 cm$^{-1}$ (FIG. 8). When the same surface was brought in contact with a polar environment (acetonitrile or water), the molecules straightened up, thereby exposing their polar end groups to the solvent. Accordingly, SFG signals associated with the CH$_2$- groups were no longer detected. For the dense SAM, structural reorganizations were far less pronounced and were in accordance to previous findings (Stole, et al., In Situ Infrared External Reflection Spectroscopy As A Probe Of The Interactions At The Liquid-Solid Interface Of Long-Chain Alkanethiol Monolayers At Gold. *Langmuir* 6, 1199-1202, 1990). We then concluded that the chain mobility is sufficient to undergo significant reorientations and assessed whether an electrical potential can similarly induce switching.

In a basic model, negatively charged end groups might act as dynamically mobile acceptors dictating reorientation of the molecules. If a change in the monolayer structure occurs upon transition of the system from a neutral to an electrified state ( N→E ), the change in Gibbs free energy of the monolayer must be negative and can be described as follows:

$$\Delta g_{total}|_{N\to E} = \Delta g_{int}|_{N\to E} + \Delta g_{sur}|_{N\to E} + g_{ele} \quad [1]$$

where $\Delta g_{int}$ is the change in the Gibbs free energy associated with internal reorganization of the molecules, $\Delta g_{sur}$ reflects the intermolecular interactions of the hydrocarbon chains and their interactions with the surrounding solvent molecules, and $g_{ele}$ describes the electrostatic component associated with attractive forces between the gold surface and the carboxylate groups. Since steric hindrance between the chains is minimal in the low-density SAM, gauche conformations associated with chain bending mainly account for $\Delta g_{int}$, which can be approximated as 0.9 nkT with n being the number of gauche-oriented bonds (Aydogan, et al., A Molecular-Thermodynamic Model For Gibbs Monolayers Formed From Redox-Active Surfactants At The Surfaces Of Aqueous Solutions: Redox-Induced Changes In Surface Tension. *Langmuir* 15, 722-730, 1999). $\Delta g_{sur}$ primarily originates from exposure of methylene groups to the surrounding aqueous environment which were embedded in the hydrophobic environment prior to application of electrical potential. This term is approximated by 1.5 mkT, where m is the number of methylene groups exposed to the aqueous surrounding due to application of electric field (Abraham, Thermodynamics Of Solution Of Homologous Series Of Solutes In Water, *J. Chem. Soc., Faraday Trans.* 1 80, 153-181, 1984). Assuming further that at least two bonds need to be gauche oriented in order to observe a detectable change in contact angle, the required contribution from the electrostatic field based on equation [1] is $|g_{ele}|>4.8$ kT. The electrostatic contribution of the free energy can be approximately described by $e\psi_o$, where e is the electronic charge and $\psi_o$ is the surface potential (Aydogan, 1999). Our calculations indicate that a potential above about +150 mV (−118 mV w.r.t. SCE) is required to satisfy the condition of molecular reorientation stated above.

Figure 9A:
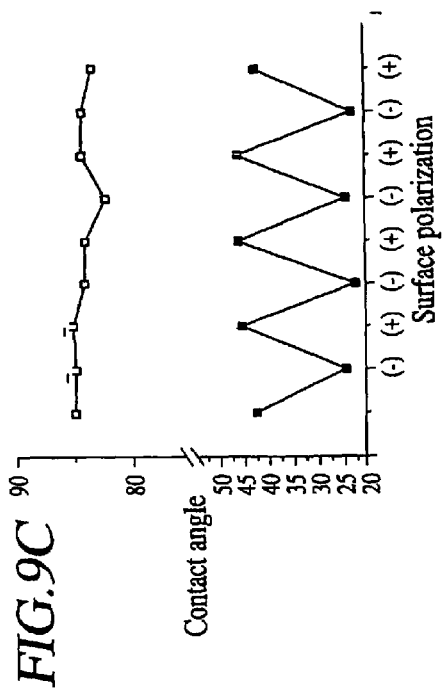
FIG. 9 shows the relative SFG intensities of the symmetric (filled symbols) and asymmetric (open symbols) $CH_2$-modes for switchable (A) and dense (B) assemblies as measured in $d^3$-acetonitrile (0.1 M CT) when a potential of +23 mV w.r.t. SCE was repeatedly applied to the system. Advancing (open symbols) and receding (full symbols) contact angles for the switchable (C) and dense (D) SAMs were determined while the potential was switched four times between +80 and −300 mV w.r.t. SCE.
Figure 9C:
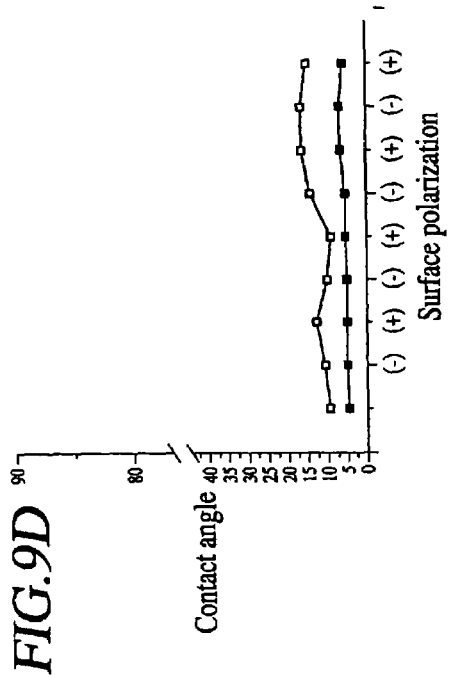
Figure 9B:
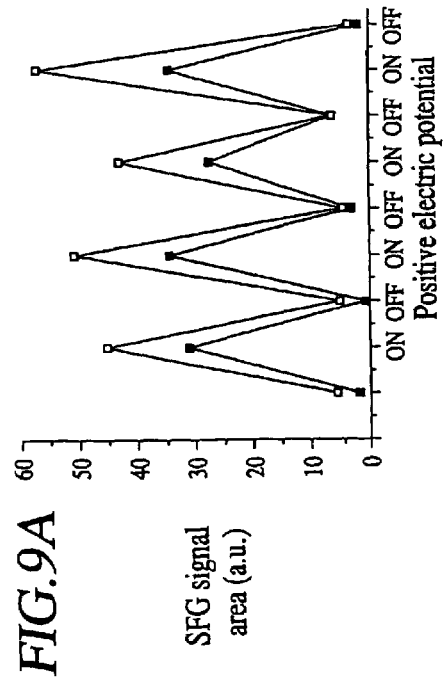

A SFG spectrometer equipped with an electrochemical quartz cell (Baldelli, et al., Sum Frequency Generation Of CO On (111) And Polycrystalline Platinum Electrode Surfaces: Evidence for SFG invisible surface CO. *J. Phys. Chem.* 103, 8920-8925, 1999) was used to assess this hypothesis. Without applied electrical potential (FIG. 4A), the SFG spectra recorded in acetonitrile (0.1 M Cesium trifluoromethanesulfonate (CT)) were featureless in the range between 2820 and 2940 cm.$^{-1}$ signifying straight molecular conformations of an all-trans orientation. Slightly positive polarization of the gold surfaces (0 to 23 mV w.r.t. SCE), however, initiated a simultaneous switching of the molecules indicated by characteristic $CH_2$-modes at wavelengths of 2855 and 2925 cm$^{-1}$. These signals demonstrate the presence of gauche-conformations in the molecules implying that the molecules bend their negatively charged end groups toward the positively charged gold surface (FIG. 1). After the positive potential decayed, the low-density SAM returned into an assembly of straight molecules with all-trans orientation, as SFG signals of the $CH_2$-groups were no longer detected (FIG. 9A). Switching was reversible with intensities of the SFG signals being nearly constant as the electrical potential was repeatedly applied. Conversely, the dense SAM did not show reorientations induced by an applied electrical potential, as the SFG signals remained unaltered when potential was applied (FIG. 9B). In other words, only the low-density SAM was reversibly switched between a straight-chain state and a bent-chain state exposing molecular moieties of ambivalent polarity on the surface.

We then addressed the question whether the observed rearrangements can actually amplify into macroscopically detectable changes in surface properties. The data of FIG. 9C show that there is indeed a significant switching of the receding contact angles as the surface polarization is alternately changed. Contact angles with an aqueous solution of CT (0.1 M, pH 11.5) were measured in air using a goniometer (VCA-2500XE, AST) equipped with an electrometer (6517A, Keithley Inst.) and a carbon fiber microelectrode (Kation Scient.). Contact angles averaged at least 100 data points of nine samples with maximum errors of ±3°. Applied electrical potentials were within the potential window of greatest stability for SAMs of alkanethiolates on gold (Everett, et al., Factors That Influence Stability Of Self-Assembled Organothiols On Gold Under Electrochemical Conditions. *Anal. Chim. Acta* 307, 253-268, 1995; Finklea, et al., Blocking Orientated Monolayers Of Alkyl Mercaptans On Gold Electrodes. *Langmuir* 3, 409-413, 1987) and thus electrochemical desorption can be excluded. In addition, SAMs were examined for chemical integrity and deprotonation by means of IR spectroscopy after an electrical potential was applied. The lines in FIG. 9 are drawn as a guide to the eye.

Figure 9D:
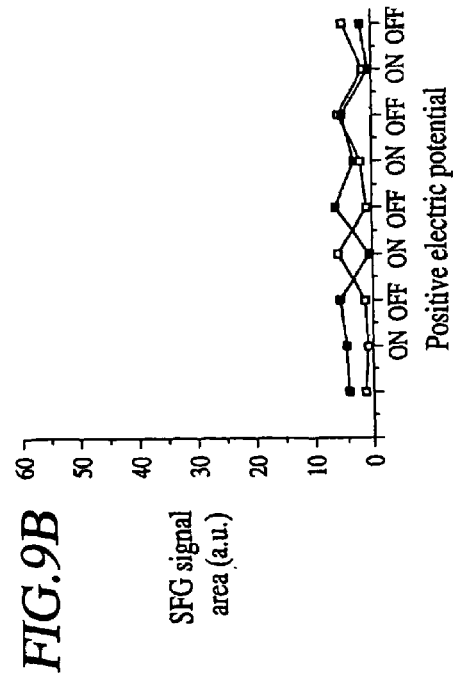

While the advancing angle was independent from the applied potential, the receding angle showed a sharp step whenever the polarization of the surface was changed (filled squares in FIG. 9C). As the latter reflects transitions in the system exposed to solvent, we conclude that the switching is necessarily associated with solvation of the surface. Furthermore, the step in contact angle was a reversible phenomenon as the assembly was switched several times between its hydrophilic and hydrophobic state (four times for the study shown in FIG. 9C). In contrast, switching was not observed for the dense SAM (FIG. 9D). Since electrochemically induced protonation of the SAM should affect both SAMs similarly, this aspect cannot account for the observed switching in contact angle. In addition, experiments were conducted at pH 11.5 to permanently avoid protonation. These findings in combination with the SFG results reveal that at each polarization state, a different aspect of the amphiphilic molecules is dominant and imprints its characteristics onto the macroscopic system resulting in a change in contact angle.

In summary, a surface switch enables reversible dynamic control of a microscopic surface environment. These findings may have implications in regulation of key macroscopic properties such as wettability, adhesion, friction, or biocompatibility. The design of amphiphiles, which cause more profound amplification of the microscopic switching into macroscopic effects may allow for engineering of novel devices with applications in areas such as microfluidics, microengineering of smart templates for bioseparation or data storage, or the microfabrication of controlled-release devices.

EXAMPLES

Optical Switches

The techniques of the invention may be used to produce optical switches. There are two major applications for optical switches, cross connects and add drop multiplexes. The required characteristics are generally similar for the two different applications. A cross connect is a device with a large number of input and output ports (several thousands in the future) where each input port can be switched to each output port. Each fiber connected to an input port can contain one or multiple wavelengths, but the device itself only switches all wavelengths in each input to the same output port without any wavelength selection or dependence. An add drop multiplex on the other hand drops and or adds selected wavelengths from one fiber. In the future, the number of wavelengths within a fiber will range from about 12 up to 80 or 160 (depending on where in the network the device sits). The ultimate add drop multiplex would have the demultiplexing (wavelength selection) and the switching in and out of channels integrated into one device. As demand for new fiber optic devices for data transfer increases, it is desirable to produce cheaper switches exhibiting lower losses and enhanced scalability.

Figure 10A:
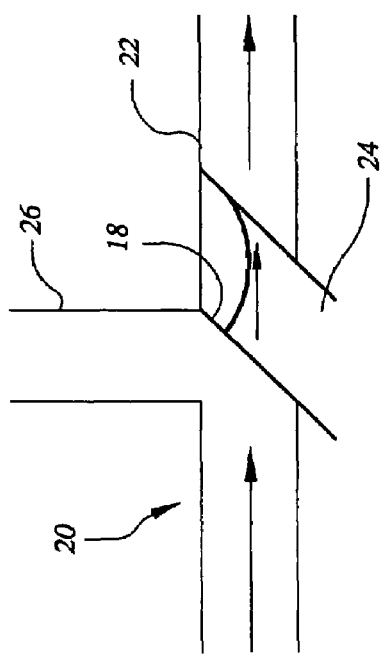
FIG. 10 is a schematic of the core unit of the disclosed fiber-optical switch in transmission mode (A) and reflecting mode (B)
Figure 10B:
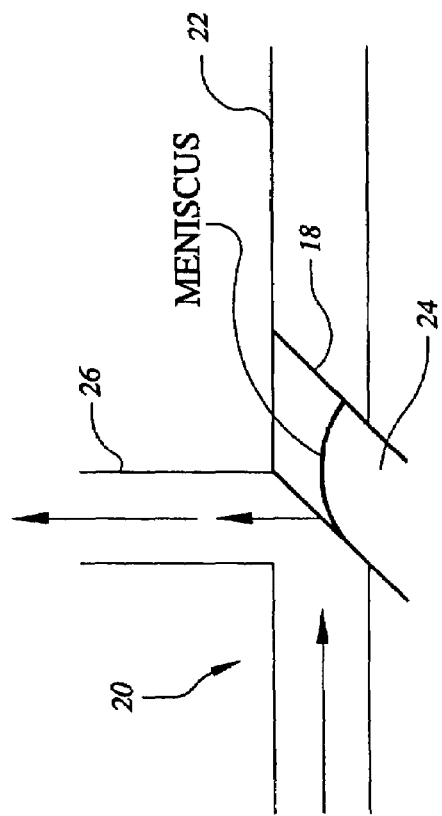

The surfaces of the invention may be exploited to produce a micro-fluid based switching cell being characterized by a gap 18 between two wave-guides 20 and 22 that crosses an optical wave-guide at a 45-degree angle (FIG. 10). The gap 18 is optionally filled with a medium 24 (preferably a liquid). The medium 24 has an index of refraction identical or close to that of the wave-guides. In the transparent or transmission state, the gap 18 contains the medium and (nearly) all the light of the incoming guide traverses the medium along the axis of the guide (FIG. 10A). In the reflection mode, the gap 18 is filled with air. Total internal reflection occurs and the light of the incoming guide is directed at right angles away from the axis of the incoming guide 20 towards a second outgoing wave guide 26 (FIG. 10B). Placing the second wave-guide perpendicular 26 to the incoming guide 20 and intersecting the first wave guide 22 at the gap forms a crossbar switch. This switching cell can be triggered between the transmission and reflection state by moving the meniscus of the medium into or away from the direction of the incoming light. Movement of the meniscus is achieved by manipulating its interaction with the interior surface of the gap. The interior surface is prepared according to the techniques of the invention to reversibly switch between hydrophilic and hydrophobic states. Favorable stimuli to induce switching include electric force fields or UV light. No power is required to hold the switch in the most recent state.

A hydrophobic interior surface will undergo favorable interactions with a hydrophobic medium (most of the potential media matching suitable reflection indices are hydrophobic) causing the meniscus of the medium to travel into the gap. Incoming light will travel through the gap 18 without any reflection. This state corresponds to total transmission. In contrast, switching the interior surface to hydrophilic will cause the medium to minimize its free surface area. In this stage, the gap will be filled with air, corresponding to total internal reflection. The incoming light will travel toward the second perpendicular wave-guide 26.

These switches have several advantages that recommend them for use in fiber optic devices. Such a switch is easily integrated with other components because silica on silicon structures can accommodate waveguides on the same substrate. Electrical components are also easily integrated with the switch, facilitating low cost, large scale fabrication. Switching between the two states is simple, and large amounts of power are not required to maintain the system in either a switched or a non-switched state, minimizing power consumption and possibly wear. These switches can be made very small, allowing a large number of switches per unit volume. Because the medium may have the same the refraction index as the glass fiber, a switch can be produced that exhibits no loss in the transmission state and minimal loss in the reflective state. The primary limitation to switching speed is the movement of the medium. While the surface properties probably switched within a few nanoseconds, the switching time is estimated in the microsecond range. Only a few watts or less are required to operate the switch, enabling low temperature use. Alternatively, the device may be used in a temperature range that is optimized for another device in the system. The disclosed device does not require a specified temperature range to operate and presents few heat dissipation issues. Cross-talk between different wave lengths in a light beam is expected to be minimal but the architecture of the device should be optimized to minimize reflection back into the fiber. The low losses enable the switch to be used in applications requiring a large number of outputs. Small losses are required because these losses are multiplied when a large number of two by two switches are cascaded to provide the desired switching capability. The device has a low polarization dependent loss, and the difference in attenuation between different polarization modes should not be more than a few percent. Because of the simple design, losses due to manufacturing errors are also expected to be low. The wavelength dependence of the device is also expected to be low with respect to the fraction, transmission, and reflection, depending on the medium that is used.

Other techniques besides surface manipulation may be exploited to manipulate the meniscus of the medium in a gap into or away from the direction of an incoming light beam. Other triggers might include the change of volume in the gap, enabled by adding a reversibly expandable material to the surface of the gap. Furthermore, triggering free surface energy by surfactants that can be reversibly activated may be suitable for manipulating the medium as well.

Drug Delivery

Figure 11:
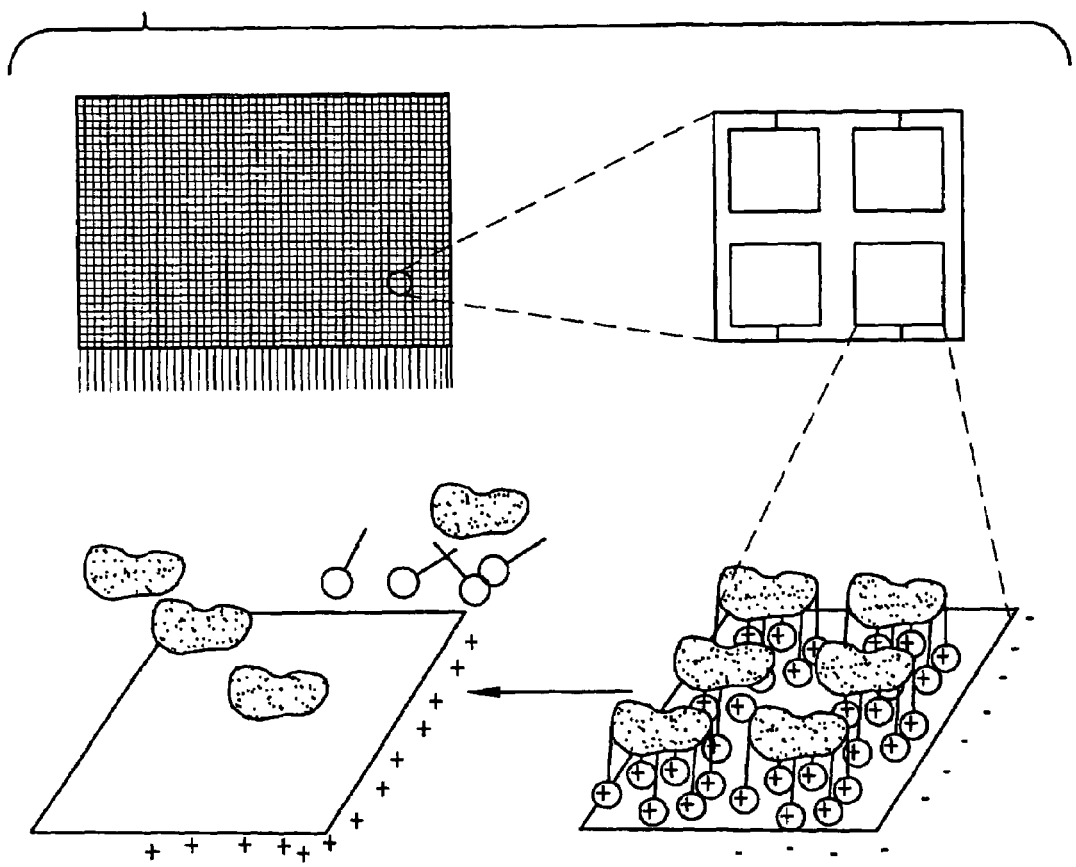
FIG. 11 depicts a drug delivery system exploiting the surface switching of an embodiment of the invention controlled by electrical modulation.

The surfaces of the invention may also be used for delivery of drugs, small molecules, biomolecules, bioactive agents, or other agents. For example, nanolayers according to the invention may be used in pharmacy on a chip applications, such as those described in U.S. Pat. No. 5,797,898 to Santini. A drug, small molecule, biomolecule, bioactive agent, or other material to be released from the chip is deposited onto a specific portion of the chip, where it is retained by a non-covalent interaction with a nanolayer deposited on the chip (FIG. 11). For example, if a drug is negatively charged, a molecular assembly having an amine group in one of the information carriers may be used to retain this small molecule. Application of a negative charge to the substrate will cause the molecular assembly to fold over and the amine to interact with the negatively charged surface, freeing the drug and allowing it to be released from the chip. Alternatively, an amphiphilic group may be used to retain a small molecule. The small molecule may be retained in the bowl or sandwich depicted in FIGS. 4 and 5 or may be retained by the negative or hydrophobic sides of the amphiphile depicted in FIG. 2.

The chip may be reused several times simply by depositing fresh supplies of the small molecule or other material on the appropriate sections of the chip. For example, the chip may be charged with one or more small molecules by dipping it into a solution containing the desired molecule and adjusting the surface charge to present the proper conformation state of the nanolayer to the solution. Sufficient time is allowed for the small molecule to be retained by the desired portions of the chip, which is then removed from the solution and rinsed to remove non-specifically retained material. The process may be repeated depending on how many different small molecules the chip will release.

Such chips may be used to control the release of a single small molecule, biomolecule, or bioactive agent, via application of a charge to specific sections of the chip over time. Gradually, all of the sections of the chip are charged and the small molecule, biomolecule, or bioactive agent is released. Alternatively, different sections of the chip may retain different chemical species. For example, if it is desired to release an anti-inflammatory agent, followed by an antibiotic or other drug, the anti-inflammatory may be deposited on portions of the chip that are connected to a circuit that charges those portions of the chip first.

Exploiting Simultanous Dual Surface Properties—Materials Separation and Biosensors The low density monolayers of the invention provide two surfaces to a surrounding medium. Larger macromolecules in the medium interact with the surface defined by the monolayer, while small ions may interact with the substrate surface. For example, this may be exploited to passivate surfaces for use in biological media. It may be desirable to maintain access to the surface, for example, of a silicon chip or gold electrode, while preventing deposition of proteins directly on the substrate surface. Loosely packed nanolayers will prevent proteins from depositing on the surface but allow atoms such as chloride through. This enables electrochemical reactions to be conducted on the surface of in vivo devices. This may be exploited in both the biosensors described below and applications which rely on the dissolution of a metal film for example, to release a material disposed in a chamber covered by the film (see U.S. Pat. No. 5,797,898 to Santini). In another embodiment, a low density monolayer may be deposited on a long term implant such as an intravenous shunt or internal prosthesis to prevent the absorption of proteins or the formation of clots on the surface. Control of surface absorption is also useful in non biological applications. The surfaces of the invention may be used to adjust the properties of channels in microfluidic applications to reduce the friction between a flowing fluid and the channel or to prevent the build up of deposits within the channels.

As noted above, the surfaces of the invention may be used as biosensors. Large molecules such as proteins will be unable to penetrate the monolayer, while smaller atoms such as ions or gas molecules will penetrate through the monolayer and reach the surface where its interaction with the surface may be detected and reported to a user. Sensors may also be used to detect specific nucleotides or polynucleotides in genetic screening. The sensors may be built on a microscopic scale, enabling large numbers to be deposited on a single substrate.

The dual surface properties of the low density nanolayers also suggest their use in chromatographic applications. The low-density nanolayer acts as a filter that allows some materials to penetrate between the chains, while larger molecules such as proteins are unable to access the surface. In one embodiment, the nanolayers are deposited on particles and placed in a column. As a mixture of larger and smaller molecules is passed through the column, they will be separated by size. Larger molecules will pass more quickly through the column because they cannot fit between the chains and interact with the surface. On the other hand, smaller molecules may interact with the chains and get tangled therein via hydrophobic interactions. To increase the interaction of the molecule with the nanolayer, a polar or charged group may be inserted into the middle of the tether. The extent of the interaction may be tuned by using molecules of different lengths for specific separations. The surface may be adapted to filter impurities from proteins or to separate different proteins from each other. For example, the surface may be tailored to interact selectively with one protein in a mixture.

Surfaces for chromatography may be exploited for protein separation and purification or even for filtration techniques such as dialysis. Indeed, the switchable nature of these surfaces enables the filters to be recharged by switching the conformation state of the nanolayer. Preferably, the surface properties of the second conformation state repel the proteins or other molecules that were previously adsorbed on the surface. These may be flushed from the filter and analyzed.

Electronic and Physical Applications

A variety of electronic applications may also exploit the techniques of the invention. For example, the two conformations of the nanolayers can be adapted to store data. For example, the external stimulus may cause the surface to register "on" or "1", while the relaxation of the surface may correspond to "off" or "0". These surfaces may thus be used as organic "transistors". Use of soft lithographic techniques to form the surface would enable high resolution of individual "bits", increasing the density of a device. The device may be rendered completely polymeric by depositing the nanolayer on a conductive polymer.

Figure 12:
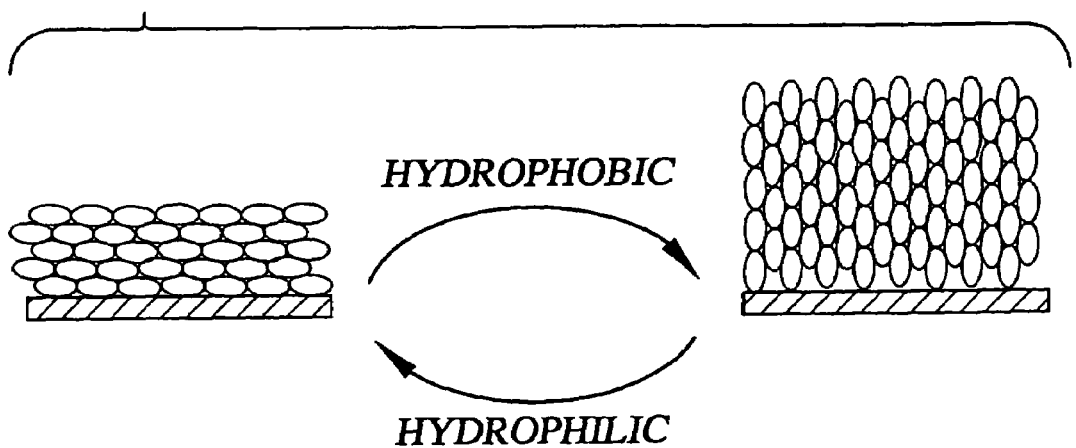
FIG. 12 depicts an application of an embodiment of the invention in which the switchable surface is used to change the orientation of a liquid crystal.

Optoelectronic applications may also exploit the inventive surfaces. The orientation of liquid crystal materials depends on their interaction with the substrate. The liquid crystals adopt a relatively consistent orientation with respect to one another. However, their orientation with respect to a substrate is determined by the interaction of the surface chemistry of the substrate with the immediately adjacent layer of liquid crystals. For example, a liquid crystal may adopt one orientation on a hydrophilic substrate and a second orientation on a hydrophobic substrate (PCT Publication No. WO99/63329, published Dec. 9, 1999). Using the techniques of the present invention, the orientation of a liquid crystal layer on a surface may be altered by switching the conformation state of a nanolayer disposed on the surface. In one embodiment (FIG. 12), a liquid crystal layer adopts one orientation when the nanolayer is in a hydrophilic conformation state; changing the conformation state of the nanolayer also causes orientation of the liquid crystal to change. Amplification of the microscopic change in surface properties is detectable using visible light, which will interact differently with the liquid crystal in its two orientations. Both thermotropic and discotic liquid crystals may be manipulated using the nanolayers of the invention (see, Boden, et al., Triphenylene-based Discotic Liquid Crystals As Self-Assembled Monolayers, *Langmuir,* 15, 3790-3797, 1999). Such techniques may be used to store, deliver, transmit, or otherwise manipulate information.

Switchable surfaces may also be used to prepare reusable surfaces. For example, if the surface of a printable medium is coated with a nanolayer according to any of the embodiments of the invention, it may be erased simply by switching the conformation state of the nanolayer. The printed material, e.g., ink or toner, will be repelled from the medium as the molecular assemblies shift conformations. Alternatively, a surface in a clean room may be provided with a monolayer to help it repel dust or other particulates. Material that settles on the surface will be dislodged as the monolayer switches conformations and will be more easily carried to the room's filtration systems. Surgical theaters, research laboratories, kitchens, and other areas where clean surfaces are desirable provide other applications for the surfaces disclosed herein.

Biological and Chemical Applications

The techniques of the invention may also be used to control chemical reactions. For example, the nanolayers on a surface may to control access of reactants to a catalyst deposited on the substrate. When the molecular assemblies in a single chain system are upright, the reactants can fit between them and reach the substrate; when the molecular assemblies bend over, they block access to the substrate. The nanolayer and catalysts may be patterned over a circuit that allows only certain regions to be accessed by the reactants. Alternatively, the nanolayer may be used to alter the local pH or ionic strength of the reaction environment, enabling the user to control reaction rates. Patterned nanolayers will enable several reactions to proceed simultaneously and selectively in the same solution.

The patterned nanolayers also provide nucleation sites for crystal growth. Deposition of both inorganic and organic materials, e.g., proteins, depends on the template on which they are deposited. The small "bits" described above also allow high-resolution two-dimensional control of nucleation. The nanolayers may be used to nucleate complex three-dimensional microstructures. Crystals of different compositions may be grown simultaneously on a single template by varying the composition and conformation state of the nanolayers to favor nucleation of specific materials. In addition, temporal as well as spatial control of the template may allow a user to manipulate the growth process to generate crystals of varying microstructures or with thermodynamically unfavorable atomic or molecular arrangements.

The surfaces of the invention may also be used to facilitate the reversible attachment of cells. Cells are typically cultured in dishes or wells that are coated with materials to which the cells adhere. However, to use the cells in other applications, they must be released from the surface. If a nanolayer has an information carrier which is favorable for cell adhesion, the cells may be cultured on the nanolayer and then easily released at an appropriate time by changing its conformation.

Likewise, the surfaces of the invention may be used to detect small concentrations of an analyte. A fluid that is being analyzed may be passed over a nanolayer having an information carrier to which the analyte will bind or adsorb. The nanolayer may be used to concentrate the analyte for easier detection or to detect small quantities of the analyte. The analyte may be detected directly, or the information carrier may have an affinity for an intermediate agent that has an affinity for the analyte and exhibits a detectable property (e.g., a specific emission or absorption wavelength) when it binds or ligates the analyte. In addition, the techniques of the invention may be used to detect an analyte in real time without modifying the concentration of the fluid. By periodically changing the conformation of the nanolayer, the analyte will be released from the detector back into the fluid.

Absorption and Desorption in Response to an External Stimulus FIG. 2 depicts a surface that switches properties via a change in electron distribution and adsorption of a surfactant from a surrounding medium. Nanolayers comprising biomolecules may also be used to exploit absorption and desorption techniques. For example, allowing a ligand, biomolecule (e.g, an antibody), small molecule, bioactive agent, or ionic species bind with a protein in a nanolayer may cause a change in conformation of the protein. The change in conformation will cause the protein to expose different amino acids having different side chains at the surface, allowing detection of the antibody (in a medical sensor) or simply providing a surface having different properties. Applying a charge to the substrate will cause the protein to alter its conformation and release the bound molecule. Single strand polynucleotides in a nanolayer will also coil differently once they bind with a complementary strand.

Photolithography

The techniques of the invention may be used to pattern a surface. Current soft lithographic techniques employ a patterned silicon rubber stamp that transfers a chemical species to a surface. The resolution of the pattern is determined by the resolution of the techniques used to pattern the stamp. Typical stamps are made by creating a pattern of troughs in a piece of silicon using standard lithographic techniques and casting the stamp over the resulting silicon mold. The surfaces of the invention may be used to create higher resolution patterns using photolithographic masks, without the need to process a piece of silicon. A film that changes conformation when exposed to high energy electromagnetic radiation, e.g., laser light, is deposited on the desired substrate according to the techniques of the invention. A mask having the desired pattern is placed over the film, which is then irradiated. The resolution of the resulting pattern depends only on the resolution of the mask. The mask may also be positioned optically, increasing the accuracy of the alignment of the mask and the position of the pattern on the substrate. In one embodiment, the two conformations of the film define hydrophobic and hydrophilic surface properties. Even on high density arrays, the high resolution film could isolate fluid droplets from each other in microfluidic applications.

Microfluidics

The switchable surfaces of the invention may also be used to direct fluids or modify the concentrations of fluids in microfluidic applications. For example, a capillary lined with a film according to the invention may be exploited to control the direction or the speed of flow through a system. For example, a fluid will flow at different rates through a channel depending on its affinity for the wall. Regions for which the fluid has lower and higher affinity may be mixed to create turbulence due to the fluctuations in flow rates. In some applications, the direction of flow may be controlled by adjusting the conformation of the film.

The techniques of the invention may also be used to dynamically control the pattern of fluid channels on a surface by adjusting the hydrophobicity of different regions to form channels and walls according to a desired pattern. The ability to change the hydrophobicity of a surface also recommends the use of nanolayers produced according to the invention for microvalves. By flipping the hydrophobicity of a portion of a channel, fluid flow through the channel will be stopped. Instead, the fluid will bead at the edge of the flipped portion. Reversing the conformation of the nanolayer a second time will allow fluid to pass through the channel without interruption. The same technique may be used to stop the formation of vortices in a flowing fluid.

The nanolayers of the invention may also be used to facilitate fluid transport, for example, between an aqueous solution and a non-aqueous solution on a chip. Progressively flipping the conformation along a channel will create a conveyor for a droplet of a fluid. For example, to transport an aqueous drop, the conformation of a nanolayer may be adjusted to create a small hydrophilic spot. The conformation of the nanolayer may be continuously adjusted to move the spot along the surface. The spot itself does not move. Rather, the conformation of the nanolayer is adjusted so that a trailing portion of the spot is flipped to a hydrophobic conformation and a portion of the nanolayer just ahead of the leading portion of the spot is flipped to a hydrophilic conformation. The droplet will adjust its position accordingly. As the process is repeated, the droplet will be directed towards its destination. If the droplet is to be mixed with another fluid, the nanolayer under the droplet may be flipped several times to mix the droplet with the fluid. Preferably, this technique is performed in a saturated atmosphere to prevent evaporation of the droplet. In one embodiment, the droplet could be employed to transport one or more cells across a surface.

In another embodiment, a liquid may be beaded in specific areas, increasing its interaction with a particular gas. If the gas contains an analyte, then the surface may be exploited as a sensor.

Offset Printing

The techniques of the invention may also be used to fabricate plates for offset printing. A plate for offset printing is coated with a nanolayer according to the invention. The nanolayer is optically patterned, e.g., with a laser, to have hydrophobic sections corresponding to the text or figure being printed surrounded by hydrophilic portions. The plate is wet with water and then inked and the ink transferred to paper using traditional offset printing techniques. The water coats the hydrophilic portions of the plate and prevents ink from being deposited on those sections of the plate. The patterned plate is highly durable and may be handled manually. In addition, the contrast between the properties of the hydrophilic and hydrophobic portions creates sharp edges at the boundaries between them, resulting in a crisp, clean printed pattern. In one embodiment, the plate is reset in situ, e.g., during printing. As the plate is rotated, the nanolayer is patterned with a first image and inked. After the ink is transferred off the plate, the nanolayer is reset to have a uniform conformation and then patterned with a second pattern. Thus, these techniques may be used to print a series of different images instead of printing one image repeatedly. The plate may be used to reduce the cost of producing short print runs. Alternatively, the plate may be used to print an entire book or other published item instead of a portion thereof, reducing the manufacturing time by obviating collation of different portions of the book printed on different printers. In one embodiment, the conformation of the nanolayer is flipped at 830 nm or 405 nm. In a preferred embodiment, the nanolayer conformation may be switched in 20 microseconds or less to maintain a desired throughput.

Fuel Cells

The nanolayers of the invention may also be used to enhance the performance of fuel cells, especially polymer electrolyte membrane (PEM) fuel cells. The level of humidity in such fuel cells should be carefully controlled to maintain the conductivity of electricity within the cell without flooding the electrode or gas diffusion path, which would hinder the diffusion of gas and protons within the cell (Larminie, et al., *Fuel Cell Systems Explained*. John Wiley and Sons, Ltd., Chichester, England, 2000). In one embodiment, a nanolayer that is switchable between a hydrophilic and a hydrophobic conformation is disposed on or near the catalyst on either or both of the anode and cathode sides of the cell. A humidity controlling system of the fuel cell measures the relative humidity within the fuel cell and controls the conformation of the nanolayer to adjust the humidity up or down. When the cell is too dry, the nanolayer or a portion thereof is switched to its hydrophilic conformation to enhance the retention of water within the cell. In a hydrophobic conformation, the nanolayer repels water, thereby reducing the humidity within the fuel cell.

In another embodiment, the nanolayers of the invention are used to remove sulfur from the gases that supply fuel to the cell. Different hydrogen and oxygen sources have varying amounts of sulfur. The storage tank for the gas may also influence the sulfur level in the fuel. The nanolayer may be disposed at or near the catalyst or along the channels through which the fuel gases pass through the cell. In one conformation, the nanolayers have a high affinity for sulfur or species such as $SO_x$. The sulfur may be cleared from the system when the fuel cell is off by changing the conformation of the nanolayer and passing air through the cell to carry off the sulfur. In an alternative embodiment, the nanolayer retains a secondary getter layer that removes sulfur or $SO_x$ from the gas. Rather than regenerating the secondary layer, the conformation of the nanolayer is reversed to release the sulfur-laden secondary layer, following which the conformation of the nanolayer is reversed again to retain a fresh secondary layer.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of reversibly modifying a property of a surface, comprising:
depositing a nanolayer of a material on at least a first portion of a substrate; and
applying an external stimulus to the nanolayer, wherein the external stimulus is selected from the group consisting of application of a voltage, a change in an applied voltage, a change in temperature, a change in pH, exposure to UV light, exposure to electromagnetic radiation, application of a magnetic field, removal of a magnetic field, a change in capacitance, application in of an electrostatic charge, removal of an electrostatic charge, and any combination of the above such that;
when the stimulus is applied, the nanolayer shifts from a first conformation state to a second conformation state, wherein, when the nanolayer is in the first conformation state, the surface is characterized by a first adsorption affinity, and, when the nanolayer is in the second conformation state, the surface is characterized by a second adsorption affinity; and
the shift in conformation state comprises a member of the group consisting of a change from a cis to a trans configured double bond, rotating a molecular group about an axis, opening a hinged molecular group, bending a molecular chain, unbending a molecular change, flipping a molecular chain and any combination thereof.

2. The method of claim 1, further comprising causing the nanolayer to shift from the second conformation state to the first conformation state.

3. The method of claim 1, wherein the affinity is for adsorption of a member of a surfactant, water, a predetermined analyte, a biomolecule, a small molecule, and a bioactive agent.

4. The method of claim 1, further comprising depositing a second nanolayer on a second portion of the substrate.

5. A substrate having a surface with reversibility switchable properties, the surface comprising:
a nanolayer of a material characterized in that, when an external stimulus is applied, the nanolayer switches from a first conformation state to a second conformation state, wherein, when the nanolayer is in the first conformation state, the surface is characterized by a first adsorption affinity, and, when the nanolayer is in the second conformation state, the surface is characterized by a second adsorption affinity, wherein the shift in conformation state comprises a member of a change from a cis to a trans configured double bond, rotating a molecular group about an axis, opening a hinged molecular group, bending a molecular chain, unbending a molecular chain, flipping a molecular chain, and any combination thereof; and wherein, the external stimulus is selected from the group consisting of application of a voltage, a change in an applied voltage, a change in temperature, a change in pH, exposure to UV light, exposure to electromagnetic radiation, application of a magnetic field, removal of a magnetic field, a change in capacitance, application in of an electrostatic charge, removal of an electrostatic charge, and any combination of the above.

6. The substrate of claim 5, wherein the affinity is for adsorption of a member of a surfactant, water, a predetermined analyte, a biomolecule, a small molecule, and a bioactive agent.

7. The substrate of claim 5, wherein the external stimulus causes a redistribution of the electron density within the nanolayer.

8. A biosensor comprising the substrate of claim 5.

9. The method of claim 1, wherein the external stimulus is selected from the group consisting of exposure to a ligand, exposure to a biomolecule, exposure to a small molecule, exposure to a bioactive agent, exposure to an ion, and any combination of the above.

10. The substrate of claim 5, wherein the external stimulus is selected from the group consisting of exposure to a ligand, exposure to a biomolecule, exposure to a small molecule, exposure to a bioactive agent, exposure to an ion, and any combination of the above.

* * * * *